US010295664B2

(12) United States Patent
Valdes et al.

(10) Patent No.: US 10,295,664 B2
(45) Date of Patent: May 21, 2019

(54) ON THE MOVE MILLIMETER WAVE INTERROGATION SYSTEM WITH A HALLWAY OF MULTIPLE TRANSMITTERS AND RECEIVERS

(71) Applicant: Northeastern University, Boston, MA (US)

(72) Inventors: Borja Gonzalez Valdes, Boston, MA (US); Carey Rappaport, Wellesley, MA (US); Jose Martinez, Providence, RI (US)

(73) Assignee: Northeastern University, Boston, MA (US)

( * ) Notice: Subject to any disclaimer, the term of this patent is extended or adjusted under 35 U.S.C. 154(b) by 775 days.

(21) Appl. No.: 14/562,094

(22) Filed: Dec. 5, 2014

(65) Prior Publication Data
US 2016/0356886 A1 Dec. 8, 2016

Related U.S. Application Data

(60) Provisional application No. 61/912,630, filed on Dec. 6, 2013.

(51) Int. Cl.
| | | |
|---|---|---|
| *G01N 1/02* | (2006.01) | |
| *G01S 13/00* | (2006.01) | |
| *G01S 13/87* | (2006.01) | |
| *G01S 13/89* | (2006.01) | |
| *G01S 13/90* | (2006.01) | |

(52) U.S. Cl.
CPC ............ *G01S 13/89* (2013.01); *G01S 13/003* (2013.01); *G01S 13/878* (2013.01); *G01N 2001/024* (2013.01); *G01S 2013/9058* (2013.01)

(58) Field of Classification Search
CPC ........ G01S 13/87; G01S 13/89; G01S 13/003; G01S 13/88; G01S 13/887; G01S 13/888; G01N 2001/024
(Continued)

(56) References Cited

U.S. PATENT DOCUMENTS 3,909,827 A * 9/1975 Tricoles ................. G01S 13/89
342/179
4,975,968 A * 12/1990 Yukl ...................... G01N 22/00
324/647
(Continued)

OTHER PUBLICATIONS

Gregory Arnold; Matthew Ferrara; Jason T. Parker; Multiple-object shape and motion reconstruction with missing radar data, Proc. of SPIE vol. 8746, Algorithms for Synthetic Aperture Radar Imagery XX, 87460G (May 23, 2013).
(Continued)

*Primary Examiner* — Peter M Bythrow
(74) *Attorney, Agent, or Firm* — Hamilton, Brook, Smith & Reynolds, P.C.

(57) ABSTRACT

In some aspects, the disclosure is directed methods and systems for screening an unconstrained subject. A plurality of transmitters may be spatially distributed on two sides along a path of movement of a subject. Each of the transmitters may transmit, in sequence, radiation to be scattered from the subject. A plurality of sensors may be spatially distributed on the two sides and coherently configured with respect to the plurality of transmitters. The plurality of sensors may collect measurements of scattered radiation corresponding to the radiation transmitted by each of the plurality of transmitters. An imaging module may generate, based on the collected measurements, a two-dimensional or three-dimensional reconstruction estimate of body surface of the subject with one or more attached foreign objects.

20 Claims, 18 Drawing Sheets

(58) Field of Classification Search
USPC .......................................................... 342/359
See application file for complete search history.

(56) References Cited

U.S. PATENT DOCUMENTS

| | | | | |
|---|---|---|---|---|
| 5,455,590 | A * | 10/1995 | Collins | G01S 13/887 342/179 |
| 6,057,761 | A * | 5/2000 | Yukl | A61B 5/0507 250/358.1 |
| 6,937,182 | B2 * | 8/2005 | Lovberg | G01S 13/887 342/179 |
| 6,965,340 | B1 * | 11/2005 | Baharav | G01S 13/89 342/175 |
| 7,034,746 | B1 * | 4/2006 | McMakin | G01S 7/024 342/175 |
| 7,183,963 | B2 * | 2/2007 | Lee | G01N 22/00 342/175 |
| 7,999,922 | B1 * | 8/2011 | Cochrane | G01B 11/2441 356/3.01 |
| 8,345,918 | B2 * | 1/2013 | Fleisher | G01N 21/3581 342/22 |
| 2004/0090359 | A1 * | 5/2004 | McMakin | G01S 7/20 342/22 |
| 2004/0140924 | A1 * | 7/2004 | Keller | G01N 21/3581 342/22 |
| 2005/0110672 | A1 * | 5/2005 | Cardiasmenos | G01N 21/3581 342/27 |
| 2006/0066469 | A1 * | 3/2006 | Foote | G01S 13/003 342/22 |
| 2007/0114418 | A1 * | 5/2007 | Mueller | G01J 3/42 250/341.1 |
| 2007/0263907 | A1 * | 11/2007 | McMakin | G01S 13/887 382/115 |
| 2009/0140907 | A1 * | 6/2009 | Keller | G01N 21/3581 342/22 |
| 2009/0322873 | A1 * | 12/2009 | Reilly | G01S 7/411 348/143 |
| 2010/0214150 | A1 * | 8/2010 | Lovberg | G01K 11/006 342/22 |
| 2010/0220001 | A1 * | 9/2010 | Longstaff | G01S 7/414 342/22 |
| 2010/0295725 | A1 * | 11/2010 | Krozer | G01S 13/003 342/25 A |
| 2011/0043403 | A1 * | 2/2011 | Loffler | G01S 7/02 342/25 A |
| 2011/0080315 | A1 * | 4/2011 | Reilly | G01S 13/86 342/175 |
| 2011/0102597 | A1 * | 5/2011 | Daly | G01S 13/887 348/162 |
| 2011/0164726 | A1 * | 7/2011 | Mastronardi | G01N 23/201 378/62 |
| 2011/0261156 | A1 * | 10/2011 | Kuznetsov | G01N 22/00 348/43 |
| 2012/0105267 | A1 * | 5/2012 | DeLia | G01S 13/86 342/22 |
| 2012/0306681 | A1 * | 12/2012 | Elad | G01S 13/867 342/27 |
| 2013/0022237 | A1 * | 1/2013 | Kuznetsov | G01S 13/867 382/103 |
| 2013/0169466 | A1 * | 7/2013 | Frederick | G08B 13/248 342/22 |
| 2014/0077988 | A1 * | 3/2014 | Saito | G01S 7/41 342/27 |

OTHER PUBLICATIONS

Chen, Chia-Ping; Chen, Chu-Song; Hung, Yi-Ping. "Pixel-Based Correspondence and Shape Reconstruction for Moving Objects," IEEE 12th International Conference on Computer Vision Workshops (ICCV Workshops), pp. 1962-1969, Sep. 27, 2009-Oct. 4, 2009.

Haworth, Christopher D.; Grafulla Gonzalez, Beatriz; Tomsin, Mathilde; Appleby, Roger; Coward, Peter R; Harvey, Andrew R.; Lebart, Katia; Petillot, Yvan R.; Trucco, Emanuele. Image Analysis for Object Detection in Millimetre-wave Images, Proc. SPIE 5619, Passive Millimetre-Wave and Terahertz Imaging and Technology, vol. 117 (Dec. 8, 2004).

Simakov, Denis; Frolova, Darya; Basri, Ronen. Dense Shape Reconstruction of a Moving Object under Arbitrary, Unknown Lighting. Proceedings of the Ninth IEEE International Conference on Computer Vision—vol. 2 (ICCV '03), IEEE Computer Society, 2003.

Kidera, S.; Sakamoto, T.; Sato, T., "Accurate UWB Radar Three-Dimensional Imaging Algorithm for a Complex Boundary Without Range Point Connections," IEEE Transactions on Geoscience and Remote Sensing, vol. 48, No. 4, pp. 1993-2004, Apr. 2010.

* cited by examiner

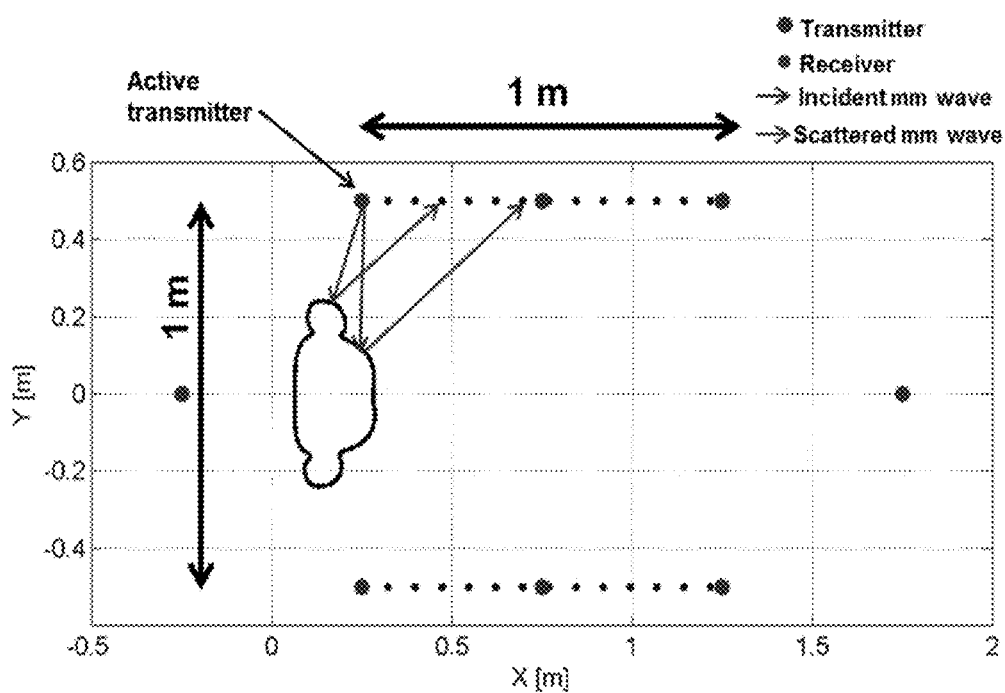
Fig. 2H
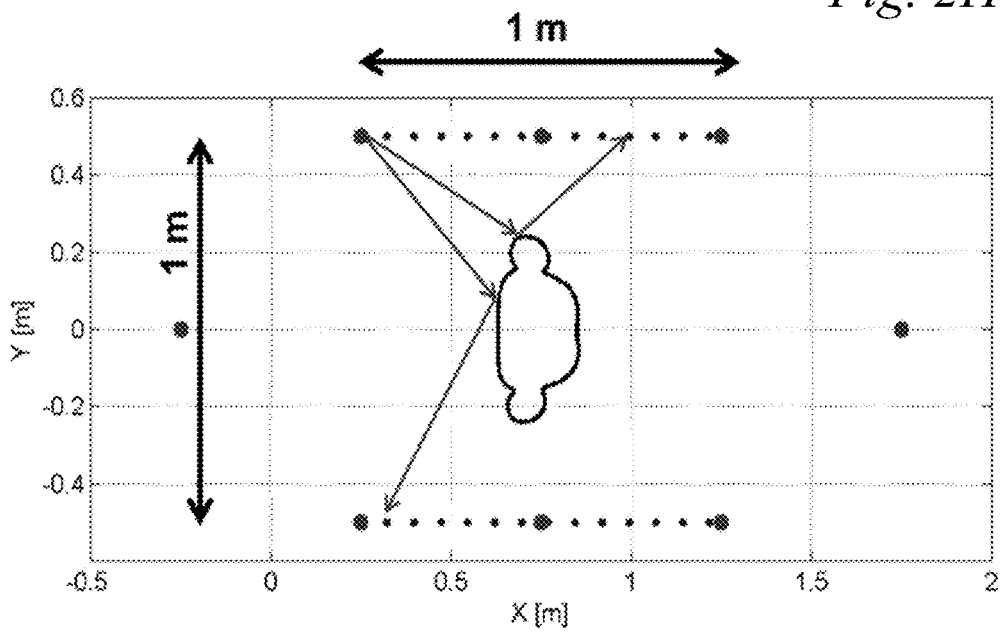

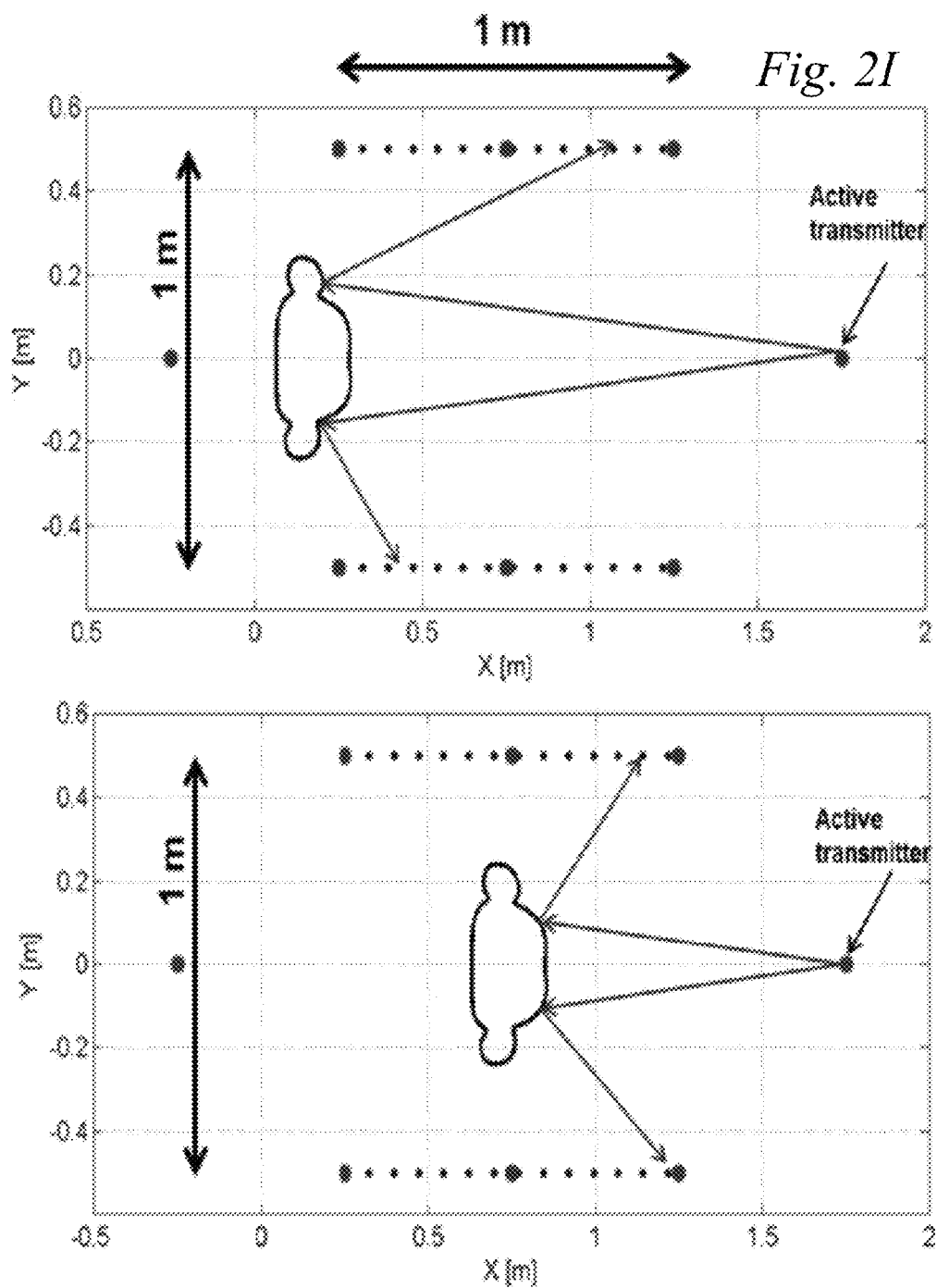

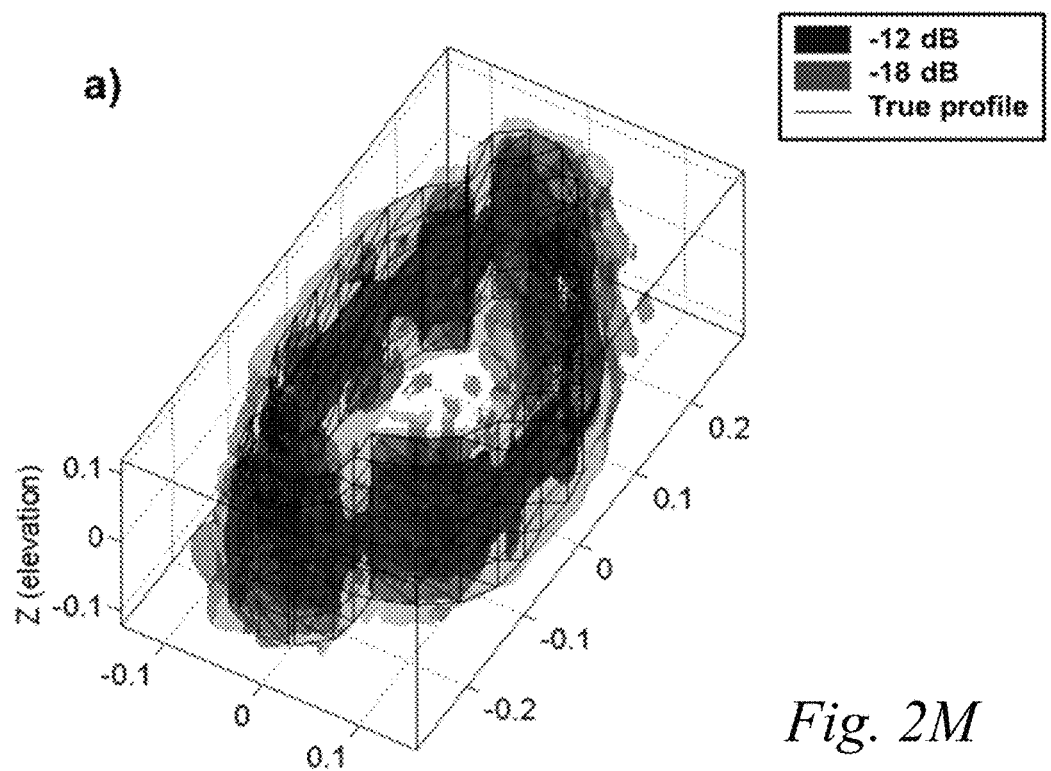
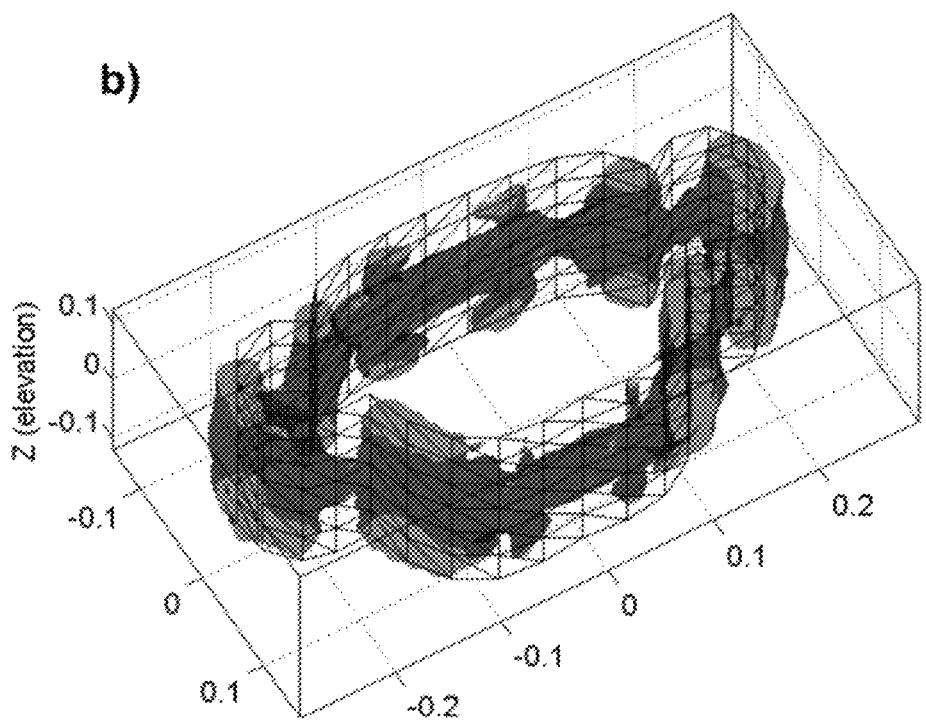
Fig. 2M

ON THE MOVE MILLIMETER WAVE INTERROGATION SYSTEM WITH A HALLWAY OF MULTIPLE TRANSMITTERS AND RECEIVERS

RELATED APPLICATION

This application claims priority to U.S. Provisional Patent Application No. 61/912,630, entitled "On The Move Millimeter Wave Interrogation System with a Hallway of Multiple Transmitters and Receivers", filed Dec. 6, 2013, which is incorporated herein by reference in its entirety for all purposes.

GOVERNMENT SUPPORT

This invention was made with government support under Grant Number 2008-ST-061-ED0001 awarded by the U.S. Department of Homeland Security (DHS). The government has certain rights in the invention.

FIELD OF THE DISCLOSURE

This disclosure generally relates to systems and methods for performing radar-based imaging or interrogation. In particular, this disclosure relates to systems and methods for screening an unconstrained subject.

BACKGROUND OF THE DISCLOSURE

In conventional systems utilizing radar imaging for surveillance and detection purposes, an object of interest may be illuminated (e.g., using millimeter wave) and the scattered field measured and processed to reconstruct a feature of the object. These systems may generate an image that profiles a detectable shape, outline and/or movement of an object or subject. Conventional radar systems, however, such as a portal-based system, constrains a subject from movement. Other conventional systems may provide an incomplete or inaccurate reconstruction estimate of body surface of a subject or object.

BRIEF SUMMARY OF THE DISCLOSURE

Described herein are systems and methods for screening an unconstrained subject, for example in security or surveillance applications. The present systems and methods may employ the use of a plurality of synchronized or coherently-configured transmitters and receivers (e.g., sensors) positioned along an expected path of motion of a subject, which can be an object or a person for example. The transmitters and receivers can be deployed or placed along a hallway for example. The transmitters and receivers may interrogate the subject from their placement positions relative to the unconstrained or moving subject at various time instances. The interrogation or screening may be radar-based, e.g., using millimeter wave radiation incident on and scattered from the subject. The transmitters may each transmit radiation in sequence, while the receivers spatially located around the subject measure the scattered radiation corresponding to each transmission. By using a multi-static configuration of transmitters and receivers, and combining information from the interrogations, different regions of the subject's body surface, including that of any attached foreign objects, can be reconstructed for example into a 3-dimensional or 2-dimensional outline or reconstruction estimate, without constraining the movement of the subject. A foreign object attached to the subject's body (e.g., hidden under clothing) can be detected from the reconstruction estimate, or from projection images generated from the reconstruction estimate.

In one aspect, the present disclosure is directed to a method for screening an unconstrained subject. The method includes transmitting, in sequence by each of a plurality of transmitters spatially distributed on two sides along a path of movement of a subject, radiation to be scattered from the subject. A plurality of sensors may be spatially distributed on the two sides and coherently configured with respect to the plurality of transmitters. The plurality of sensors may collect measurements of scattered radiation corresponding to the radiation transmitted by each of the plurality of transmitters. An imaging module may generate, based on the collected measurements, a two-dimensional or three-dimensional reconstruction estimate of body surface of the subject with one or more attached foreign objects.

In some embodiments, a first transmitter is located on a first side of the two sides along the path of movement, and may transmit radiation at a first time instance. A second transmitter may be located on a second side of the two sides along the path of movement, and may transmit radiation at a second time instance. In certain embodiments, a first sensor is located on a first side of the two sides along the path of movement, and may collect, at a first time instance, measurement of a first scattered radiation corresponding to radiation transmitted by a first transmitter of the plurality of transmitters. A second sensor may be located on a second side of the two sides along the path of movement, and may collect, at the first time instance, measurement of a second scattered radiation corresponding to radiation transmitted by the first transmitter.

In some embodiments, the plurality of sensors collects measurements of radiation scattered from the subject at a first position along the path of movement based on radiation from a first transmitter of the plurality of transmitters, and collects measurements of radiation scattered from the subject at a second position along the path of movement based on radiation from a second transmitter of the plurality of transmitters. A first sensor may collect a measurement of radiation scattered from the subject based on radiation transmitted by a first transmitter. The first transmitter and the first sensor may have a subtended angle of at least 90 degrees relative to the subject. In certain embodiments, a first sensor collects a measurement of radiation scattered from the subject based on radiation transmitted by a first transmitter. The first transmitter and the first sensor may have a subtended angle less than 90 degrees relative to the subject.

In certain embodiments, a first transmitter is located in front of the subject or behind the subject along the path of movement, and may transmit, at a first time instance, radiation incident on the subject. The plurality of sensors may collect measurements of radiation scattered from the subject corresponding to the radiation transmitted by the first transmitter.

In some embodiments, the imaging module generates a plurality of partial reconstruction estimates. Each of the plurality of partial reconstruction estimates may be generated based on measurements of scattered radiation corresponding to radiation transmitted by a respective transmitter from the plurality of transmitters. The imaging module may register a position of the subject along the path of movement with a corresponding one of the plurality of partial reconstruction estimates. The imaging module may combine the plurality of partial reconstruction estimates to generate the two-dimensional or three-dimensional reconstruction estimate.

In another aspect, the present disclosure is directed to a system for screening an unconstrained subject. The system may include a plurality of transmitters spatially distributed on two sides along a path of movement of a subject. Each of the plurality of transmitters may transmit, in sequence, radiation to be scattered from the subject. A plurality of sensors may be spatially distributed on the two sides and coherently configured with respect to the plurality of transmitters. The plurality of sensors may collect measurements of scattered radiation corresponding to the radiation transmitted by each of the plurality of transmitters. An imaging module may generate, based on the collected measurements, a two-dimensional or three-dimensional reconstruction estimate of body surface of the subject with one or more attached foreign objects.

In some embodiments, the plurality of transmitters includes a first transmitter located on a first side of the two sides transmitting radiation at a first time instance. A second transmitter located on a second side of the two sides may transmit radiation at a second time instance. In certain embodiments, the plurality of sensors comprises a first sensor located on a first side of the two sides collecting, at a first time instance, measurement of a first scattered radiation corresponding to radiation transmitted by a first transmitter of the plurality of transmitters. The plurality of sensors may include a second sensor located on a second side of the two sides collecting, at the first time instance, measurement of a second scattered radiation corresponding to radiation transmitted by the first transmitter.

In some embodiments, the plurality of sensors collects measurements of radiation scattered from the subject at a first position along the path of movement based on radiation from a first transmitter of the plurality of transmitters. The plurality of sensors may collect measurements of radiation scattered from the subject at a second position along the path of movement based on radiation from a second transmitter of the plurality of transmitters. In certain embodiments, the plurality of sensors includes a first sensor collecting measurement of radiation scattered from the subject based on radiation transmitted by a first transmitter. The first transmitter and the first sensor may have a subtended angle of at least 90 degrees relative to the subject. In some embodiments, the plurality of sensors includes a first sensor collecting measurement of radiation scattered from the subject based on radiation transmitted by a first transmitter. The first transmitter and the first sensor may have a subtended angle less than 90 degrees relative to the subject.

In certain embodiments, the plurality of transmitters includes a first transmitter located in front of the subject or behind the subject along the path of movement. The first transmitter may transmit, at a first time instance, radiation incident on the subject. The plurality of sensors may collect measurements of radiation scattered from the subject corresponding to the radiation transmitted by the first transmitter.

In some embodiments, the imaging engine generates a plurality of partial reconstruction estimates, each of the plurality of partial reconstruction estimates generated based on measurements of scattered radiation corresponding to radiation transmitted by a respective transmitter from the plurality of transmitters. The imaging engine may register a position of the subject along the path of movement with a corresponding one of the plurality of partial reconstruction estimates. The imaging engine may combine the plurality of partial reconstruction estimates to generate the two-dimensional or three-dimensional reconstruction estimate.

The details of various embodiments of the invention are set forth in the accompanying drawings and the description below.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIGS. 2H and 2I depict embodiments of a system for screening an unconstrained subject;

FIG. 2L depicts one embodiment of a system for screening an unconstrained subject;

FIG. 2M depicts examples of three dimensional reconstruction estimates;

FIG. 2O is a flow diagram of an embodiment of a method for screening an unconstrained subject.

Figure 1A:
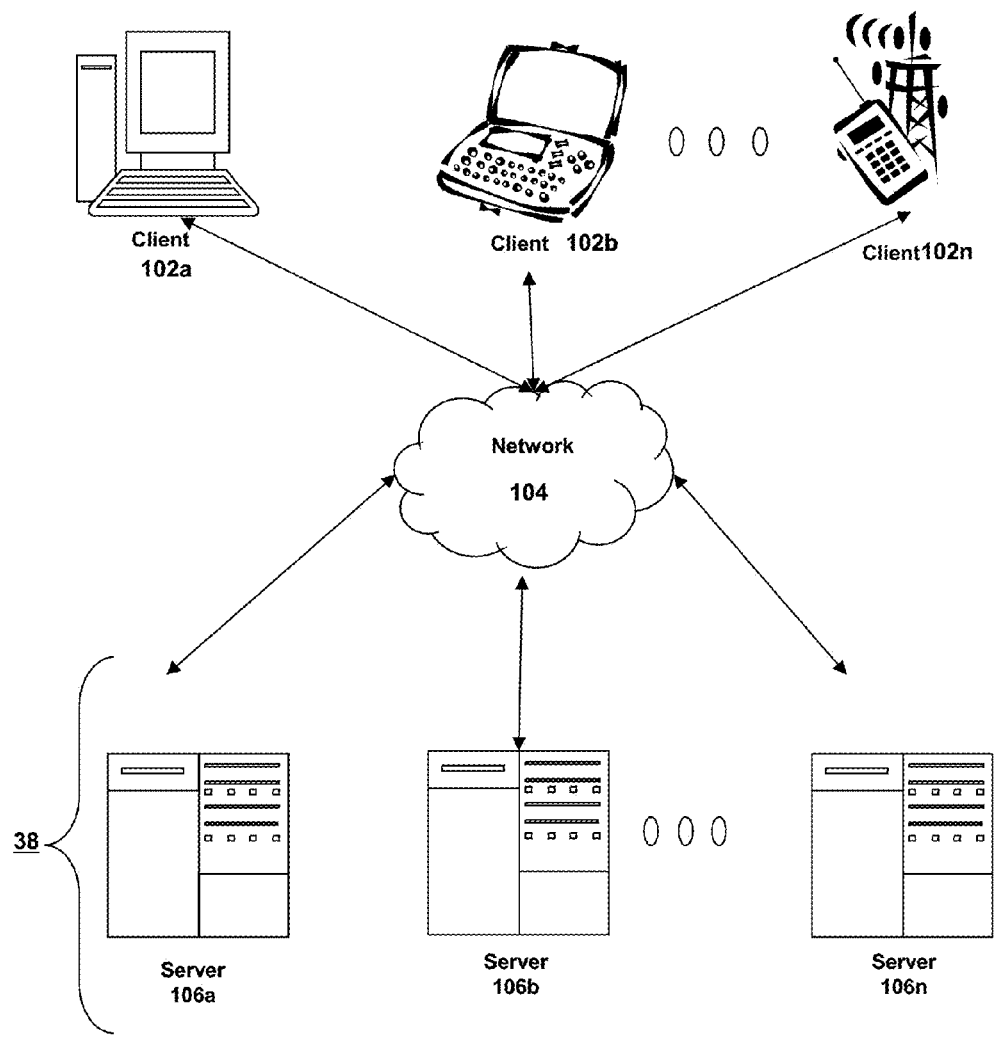
FIG. 1A is a block diagram depicting an embodiment of a network environment comprising client machines in communication with remote machines.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

For purposes of reading the description of the various embodiments below, the following descriptions of the sections of the specification and their respective contents may be helpful:

Section A describes a network environment and computing environment which may be useful for practicing embodiments described herein; and Section B describes embodiments of systems and methods for screening an unconstrained subject.

A. Computing and Network Environment

Prior to discussing specific embodiments of the present solution, it may be helpful to describe aspects of the operating environment as well as associated system components (e.g., hardware elements) in connection with the methods and systems described herein. Referring to FIG. 1A, an embodiment of a network environment is depicted. In brief overview, the network environment includes one or more clients 101a-101n (also generally referred to as local machine(s) 101, client(s) 101, client node(s) 101, client machine(s) 101, client computer(s) 101, client device(s) 101, endpoint(s) 101, or endpoint node(s) 101) in communication with one or more servers 106a-106n (also generally referred to as server(s) 106, node 106, or remote machine(s) 106) via one or more networks 104. In some embodiments, a client 101 has the capacity to function as both a client node seeking access to resources provided by a server and as a server providing access to hosted resources for other clients 101a-101n.

Although FIG. 1A shows a network 104 between the clients 101 and the servers 106, the clients 101 and the servers 106 may be on the same network 104. The network 104 can be a local-area network (LAN), such as a company Intranet, a metropolitan area network (MAN), or a wide area network (WAN), such as the Internet or the World Wide Web. In some embodiments, there are multiple networks 104 between the clients 101 and the servers 106. In one of these embodiments, a network 104' (not shown) may be a private network and a network 104 may be a public network. In another of these embodiments, a network 104 may be a private network and a network 104' a public network. In still another of these embodiments, networks 104 and 104' may both be private networks.

The network 104 may be any type and/or form of network and may include any of the following: a point-to-point network, a broadcast network, a wide area network, a local area network, a telecommunications network, a data communication network, a computer network, an ATM (Asynchronous Transfer Mode) network, a SONET (Synchronous Optical Network) network, a SDH (Synchronous Digital Hierarchy) network, a wireless network and a wireline network. In some embodiments, the network 104 may comprise a wireless link, such as an infrared channel or satellite band. The topology of the network 104 may be a bus, star, or ring network topology. The network 104 may be of any such network topology as known to those ordinarily skilled in the art capable of supporting the operations described herein. The network may comprise mobile telephone networks utilizing any protocol(s) or standard(s) used to communicate among mobile devices, including AMPS, TDMA, CDMA, GSM, GPRS, UMTS, WiMAX, 3G or 4G. In some embodiments, different types of data may be transmitted via different protocols. In other embodiments, the same types of data may be transmitted via different protocols.

In some embodiments, the system may include multiple, logically-grouped servers 106. In one of these embodiments, the logical group of servers may be referred to as a server farm 38 or a machine farm 38. In another of these embodiments, the servers 106 may be geographically dispersed. In other embodiments, a machine farm 38 may be administered as a single entity. In still other embodiments, the machine farm 38 includes a plurality of machine farms 38. The servers 106 within each machine farm 38 can be heterogeneous—one or more of the servers 106 or machines 106 can operate according to one type of operating system platform (e.g., WINDOWS, manufactured by Microsoft Corp. of Redmond, Wash.), while one or more of the other servers 106 can operate on according to another type of operating system platform (e.g., Unix or Linux).

In one embodiment, servers 106 in the machine farm 38 may be stored in high-density rack systems, along with associated storage systems, and located in an enterprise data center. In this embodiment, consolidating the servers 106 in this way may improve system manageability, data security, the physical security of the system, and system performance by locating servers 106 and high performance storage systems on localized high performance networks. Centralizing the servers 106 and storage systems and coupling them with advanced system management tools allows more efficient use of server resources.

The servers 106 of each machine farm 38 do not need to be physically proximate to another server 106 in the same machine farm 38. Thus, the group of servers 106 logically grouped as a machine farm 38 may be interconnected using a wide-area network (WAN) connection or a metropolitan-area network (MAN) connection. For example, a machine farm 38 may include servers 106 physically located in different continents or different regions of a continent, country, state, city, campus, or room. Data transmission speeds between servers 106 in the machine farm 38 can be increased if the servers 106 are connected using a local-area network (LAN) connection or some form of direct connection. Additionally, a heterogeneous machine farm 38 may include one or more servers 106 operating according to a type of operating system, while one or more other servers 106 execute one or more types of hypervisors rather than operating systems. In these embodiments, hypervisors may be used to emulate virtual hardware, partition physical hardware, virtualize physical hardware, and execute virtual machines that provide access to computing environments. Hypervisors may include those manufactured by VMWare, Inc., of Palo Alto, Calif.; the Xen hypervisor, an open source product whose development is overseen by Citrix Systems, Inc.; the Virtual Server or virtual PC hypervisors provided by Microsoft or others.

In order to manage a machine farm 38, at least one aspect of the performance of servers 106 in the machine farm 38 should be monitored. Typically, the load placed on each server 106 or the status of sessions running on each server 106 is monitored. In some embodiments, a centralized service may provide management for machine farm 38. The centralized service may gather and store information about a plurality of servers 106, respond to requests for access to resources hosted by servers 106, and enable the establishment of connections between client machines 101 and servers 106.

Management of the machine farm 38 may be de-centralized. For example, one or more servers 106 may comprise components, subsystems and modules to support one or more management services for the machine farm 38. In one of these embodiments, one or more servers 106 provide functionality for management of dynamic data, including techniques for handling failover, data replication, and increasing the robustness of the machine farm 38. Each server 106 may communicate with a persistent store and, in some embodiments, with a dynamic store.

Server 106 may be a file server, application server, web server, proxy server, appliance, network appliance, gateway, gateway, gateway server, virtualization server, deployment server, SSL VPN server, or firewall. In one embodiment, the server 106 may be referred to as a remote machine or a node. In another embodiment, a plurality of nodes 290 may be in the path between any two communicating servers.

In one embodiment, the server 106 provides the functionality of a web server. In another embodiment, the server 106a receives requests from the client 101, forwards the requests to a second server 106b and responds to the request by the client 101 with a response to the request from the server 106b. In still another embodiment, the server 106 acquires an enumeration of applications available to the client 101 and address information associated with a server 106' hosting an application identified by the enumeration of applications. In yet another embodiment, the server 106 presents the response to the request to the client 101 using a web interface. In one embodiment, the client 101 communicates directly with the server 106 to access the identified application. In another embodiment, the client 101 receives output data, such as display data, generated by an execution of the identified application on the server 106.

Figure 1B:
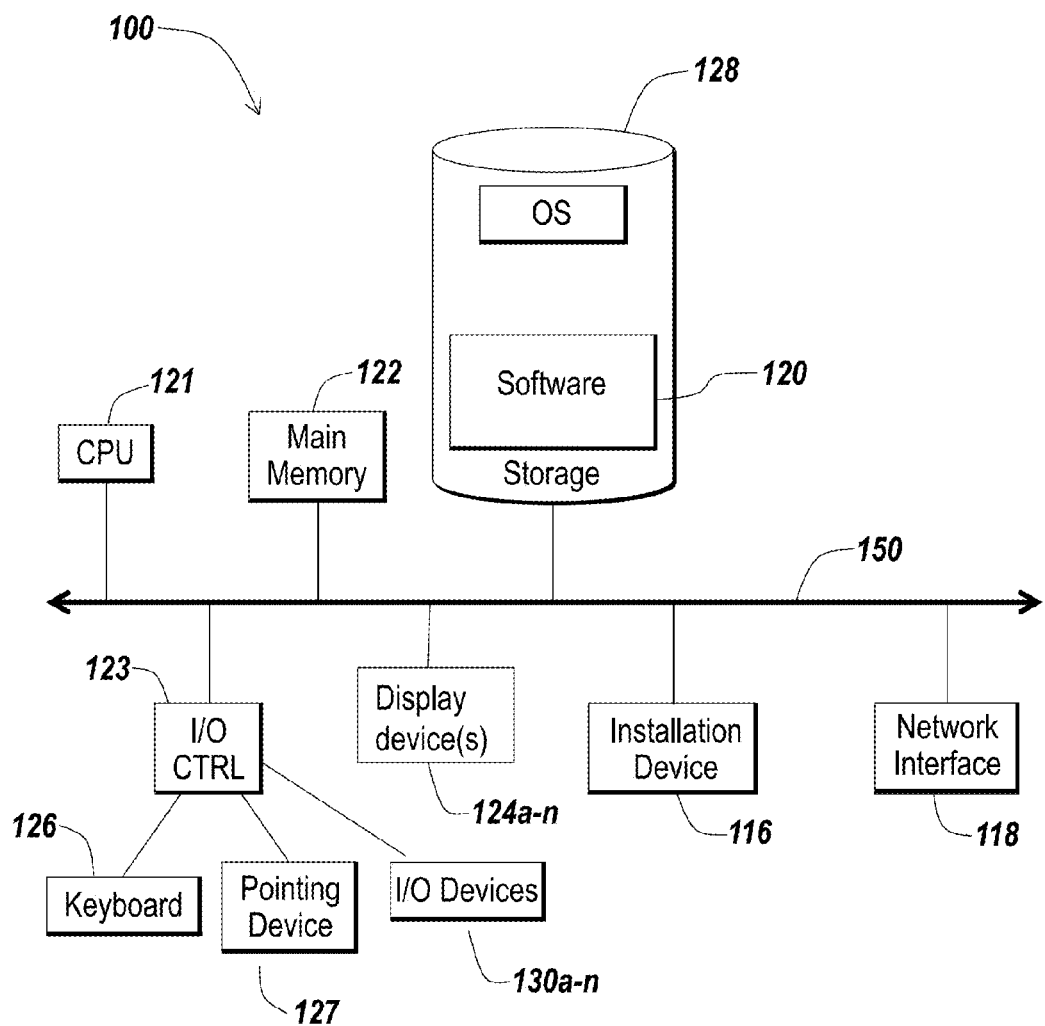
FIGS. 1B and 1C are block diagrams depicting embodiments of computing devices useful in connection with the methods and systems described herein.
Figure 1C:
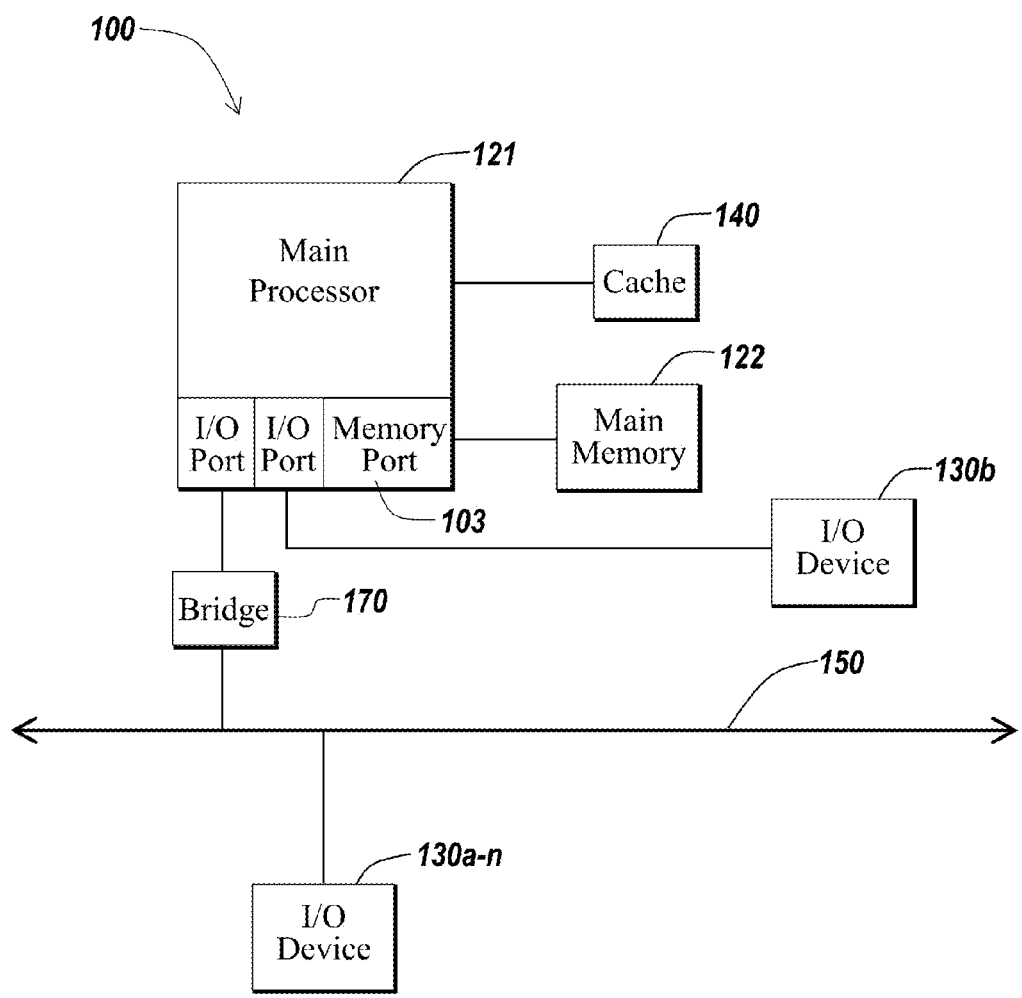

The client 101 and server 106 may be deployed as and/or executed on any type and form of computing device, such as a computer, network device or appliance capable of communicating on any type and form of network and performing the operations described herein. FIGS. 1B and 1C depict block diagrams of a computing device 100 useful for practicing an embodiment of the client 101 or a server 106. As shown in FIGS. 1B and 1C, each computing device 100 includes a central processing unit 121, and a main memory unit 122. As shown in FIG. 1B, a computing device 100 may include a storage device 128, an installation device 116, a network interface 118, an I/O controller 123, display devices 124a-101n, a keyboard 126 and a pointing device 127, such as a mouse. The storage device 128 may include, without limitation, an operating system and/or software. As shown in FIG. 1C, each computing device 100 may also include additional optional elements, such as a memory port 103, a bridge 170, one or more input/output devices 130a-130n (generally referred to using reference numeral 130), and a cache memory 140 in communication with the central processing unit 121.

The central processing unit 121 is any logic circuitry that responds to and processes instructions fetched from the main memory unit 122. In many embodiments, the central processing unit 121 is provided by a microprocessor unit, such as: those manufactured by Intel Corporation of Mountain View, Calif.; those manufactured by Motorola Corporation of Schaumburg, Ill.; those manufactured by International Business Machines of White Plains, N.Y.; or those manufactured by Advanced Micro Devices of Sunnyvale, Calif. The computing device 100 may be based on any of these processors, or any other processor capable of operating as described herein.

Main memory unit 122 may be one or more memory chips capable of storing data and allowing any storage location to be directly accessed by the microprocessor 121, such as Static random access memory (SRAM), Burst SRAM or SynchBurst SRAM (BSRAM), Dynamic random access memory (DRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Enhanced DRAM (EDRAM), synchronous DRAM (SDRAM), JEDEC SRAM, PC 100 SDRAM, Double Data Rate SDRAM (DDR SDRAM), Enhanced SDRAM (ESDRAM), SyncLink DRAM (SLDRAM), Direct Rambus DRAM (DRDRAM), Ferroelectric RAM (FRAM), NAND Flash, NOR Flash and Solid State Drives (SSD). The main memory 122 may be based on any of the above described memory chips, or any other available memory chips capable of operating as described herein. In the embodiment shown in FIG. 1B, the processor 121 communicates with main memory 122 via a system bus 150 (described in more detail below). FIG. 1C depicts an embodiment of a computing device 100 in which the processor communicates directly with main memory 122 via a memory port 103. For example, in FIG. 1C the main memory 122 may be DRDRAM.

FIG. 1C depicts an embodiment in which the main processor 121 communicates directly with cache memory 140 via a secondary bus, sometimes referred to as a backside bus. In other embodiments, the main processor 121 communicates with cache memory 140 using the system bus 150. Cache memory 140 typically has a faster response time than main memory 122 and is typically provided by SRAM, BSRAM, or EDRAM. In the embodiment shown in FIG. 1C, the processor 121 communicates with various I/O devices 130 via a local system bus 150. Various buses may be used to connect the central processing unit 121 to any of the I/O devices 130, including a VESA VL bus, an ISA bus, an EISA bus, a MicroChannel Architecture (MCA) bus, a PCI bus, a PCI-X bus, a PCI-Express bus, or a NuBus. For embodiments in which the I/O device is a video display 124, the processor 121 may use an Advanced Graphics Port (AGP) to communicate with the display 124. FIG. 1C depicts an embodiment of a computer 100 in which the main processor 121 may communicate directly with I/O device 130b, for example via HYPERTRANSPORT, RAPIDIO, or INFINIBAND communications technology. FIG. 1C also depicts an embodiment in which local busses and direct communication are mixed: the processor 121 communicates with I/O device 130a using a local interconnect bus while communicating with I/O device 130b directly.

A wide variety of I/O devices 130a-130n may be present in the computing device 100. Input devices include keyboards, mice, trackpads, trackballs, microphones, dials, touch pads, and drawing tablets. Output devices include video displays, speakers, inkjet printers, laser printers, projectors and dye-sublimation printers. The I/O devices may be controlled by an I/O controller 123 as shown in FIG. 1B. The I/O controller may control one or more I/O devices such as a keyboard 126 and a pointing device 127, e.g., a mouse or optical pen. Furthermore, an I/O device may also provide storage and/or an installation medium 116 for the computing device 100. In still other embodiments, the computing device 100 may provide USB connections (not shown) to receive handheld USB storage devices such as the USB Flash Drive line of devices manufactured by Twintech Industry, Inc. of Los Alamitos, Calif.

Referring again to FIG. 1B, the computing device 100 may support any suitable installation device 116, such as a disk drive, a CD-ROM drive, a CD-R/RW drive, a DVD-ROM drive, a flash memory drive, tape drives of various formats, USB device, hard-drive or any other device suitable for installing software and programs. The computing device 100 can further include a storage device, such as one or more hard disk drives or redundant arrays of independent disks, for storing an operating system and other related software, and for storing application software programs such as any program or software 120 for implementing (e.g., configured and/or designed for) the systems and methods described herein. Optionally, any of the installation devices 116 could also be used as the storage device. Additionally, the operating system and the software can be run from a bootable medium, for example, a bootable CD.

Furthermore, the computing device 100 may include a network interface 118 to interface to the network 104 through a variety of connections including, but not limited to, standard telephone lines, LAN or WAN links (e.g., 802.11, T1, T3, 56 kb, X.25, SNA, DECNET), broadband connections (e.g., ISDN, Frame Relay, ATM, Gigabit Ethernet, Ethernet-over-SONET), wireless connections, or some combination of any or all of the above. Connections can be established using a variety of communication protocols (e.g., TCP/IP, IPX, SPX, NetBIOS, Ethernet, ARCNET, SONET, SDH, Fiber Distributed Data Interface (FDDI), RS232, IEEE 802.11, IEEE 802.11a, IEEE 802.11b, IEEE 802.11g, IEEE 802.11n, CDMA, GSM, WiMax and direct asynchronous connections). In one embodiment, the computing device 100 communicates with other computing devices 100' via any type and/or form of gateway or tunneling protocol such as Secure Socket Layer (SSL) or Transport Layer Security (TLS), or the Citrix Gateway Protocol manufactured by Citrix Systems, Inc. of Ft. Lauderdale, Fla. The network interface 118 may comprise a built-in network adapter, network interface card, PCMCIA network card, card bus network adapter, wireless network adapter, USB network adapter, modem or any other device suitable for interfacing the computing device 100 to any type of network capable of communication and performing the operations described herein.

In some embodiments, the computing device 100 may comprise or be connected to multiple display devices 124a-124n, which each may be of the same or different type and/or form. As such, any of the I/O devices 130a-130n and/or the I/O controller 123 may comprise any type and/or form of suitable hardware, software, or combination of hardware and software to support, enable or provide for the connection and use of multiple display devices 124a-124n by the computing device 100. For example, the computing device 100 may include any type and/or form of video adapter, video card, driver, and/or library to interface, communicate, connect or otherwise use the display devices 124a-124n. In one embodiment, a video adapter may comprise multiple connectors to interface to multiple display devices 124a-124n. In other embodiments, the computing device 100 may include multiple video adapters, with each video adapter connected to one or more of the display devices 124a-124n. In some embodiments, any portion of the operating system of the computing device 100 may be configured for using multiple displays 124a-124n. In other embodiments, one or more of the display devices 124a-124n may be provided by one or more other computing devices, such as computing devices 100a and 100b connected to the computing device 100, for example, via a network. These embodiments may include any type of software designed and constructed to use another computer's display device as a second display device 124a for the computing device 100. One ordinarily skilled in the art will recognize and appreciate the various ways and embodiments that a computing device 100 may be configured to have multiple display devices 124a-124n.

In further embodiments, an I/O device 130 may be a bridge between the system bus 150 and an external communication bus, such as a USB bus, an Apple Desktop Bus, an RS-232 serial connection, a SCSI bus, a FireWire bus, a FireWire 800 bus, an Ethernet bus, an AppleTalk bus, a Gigabit Ethernet bus, an Asynchronous Transfer Mode bus, a FibreChannel bus, a Serial Attached small computer system interface bus, or a HDMI bus.

A computing device 100 of the sort depicted in FIGS. 1B and 1C typically operates under the control of operating systems, which control scheduling of tasks and access to system resources. The computing device 100 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: Android, manufactured by Google Inc; WINDOWS 7 and 8, manufactured by Microsoft Corporation of Redmond, Wash.; MAC OS, manufactured by Apple Computer of Cupertino, Calif.; WebOS, manufactured by Research In Motion (RIM); OS/2, manufactured by International Business Machines of Armonk, N.Y.; and Linux, a freely-available operating system distributed by Caldera Corp. of Salt Lake City, Utah, or any type and/or form of a Unix operating system, among others.

The computer system 100 can be any workstation, telephone, desktop computer, laptop or notebook computer, server, handheld computer, mobile telephone or other portable telecommunications device, media playing device, a gaming system, mobile computing device, or any other type and/or form of computing, telecommunications or media device that is capable of communication. The computer system 100 has sufficient processor power and memory capacity to perform the operations described herein. For example, the computer system 100 may comprise a device of the IPAD or IPOD family of devices manufactured by Apple Computer of Cupertino, Calif., a device of the PLAYSTATION family of devices manufactured by the Sony Corporation of Tokyo, Japan, a device of the NINTENDO/Wii family of devices manufactured by Nintendo Co., Ltd., of Kyoto, Japan, or an XBOX device manufactured by the Microsoft Corporation of Redmond, Wash.

In some embodiments, the computing device 100 may have different processors, operating systems, and input devices consistent with the device. For example, in one embodiment, the computing device 100 is a smart phone, mobile device, tablet or personal digital assistant. In still other embodiments, the computing device 100 is an Android-based mobile device, an iPhone smart phone manufactured by Apple Computer of Cupertino, Calif., or a Blackberry handheld or smart phone, such as the devices manufactured by Research In Motion Limited. Moreover, the computing device 100 can be any workstation, desktop computer, laptop or notebook computer, server, handheld computer, mobile telephone, any other computer, or other form of computing or telecommunications device that is capable of communication and that has sufficient processor power and memory capacity to perform the operations described herein.

In some embodiments, the computing device 100 is a digital audio player. In one of these embodiments, the computing device 100 is a tablet such as the Apple IPAD, or a digital audio player such as the Apple IPOD lines of devices, manufactured by Apple Computer of Cupertino, Calif. In another of these embodiments, the digital audio player may function as both a portable media player and as a mass storage device. In other embodiments, the computing device 100 is a digital audio player such as an MP3 players. In yet other embodiments, the computing device 100 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the communications device 101 includes a combination of devices, such as a mobile phone combined with a digital audio player or portable media player. In one of these embodiments, the communications device 101 is a smartphone, for example, an iPhone manufactured by Apple Computer, or a Blackberry device, manufactured by Research In Motion Limited. In yet another embodiment, the communications device 101 is a laptop or desktop computer equipped with a web browser and a microphone and speaker system, such as a telephony headset. In these embodiments, the communications devices 101 are web-enabled and can receive and initiate phone calls.

In some embodiments, the status of one or more machines 101, 106 in the network 104 is monitored, generally as part of network management. In one of these embodiments, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

B. Screening an Unconstrained Subject

Described herein are systems and methods for screening an object, person or region of interest, or any other subject. Applications for the present systems and methods may include, but are not limited to detection of objects, features or material, for security and surveillance purposes for example. Embodiments of the present systems and methods may be incorporated into near-field and/or far-field scanning and imaging systems, for example for deployment in airports, transportation venues, secure facilities, government buildings, sports arenas and building entrances.

By way of example, the detection and identification of objects placed or hidden under clothing has become of special interest concerning homeland security issues. High-accuracy human body torso imaging may be an effective way of determining whether a person is carrying potential threats or contraband under his/her clothing. Technologies that may be used for personnel screening include X-ray backscatter and millimeter wave scanners, as non-limiting examples. Since clothing and many other materials are transparent at millimeter wave radio frequency bands, this technology can be implemented to reconstruct an image of the body surface and any attached objects. Millimeter wave scanners may be implemented in two different modalities: passive and active. Passive scanners can create images using ambient radiation. With millimeter-wave radar (e.g. in active scanners), the object of interest may be illuminated by millimeter waves and the resulting scattered field may be measured and processed in order to reconstruct an outline, surface or volume of the object. The reconstructed outline, surface or volume is sometimes referred to as a reconstruction estimate.

In some implementations, active millimeter wave scanners are based on a portal configuration and mono-static radar technology (e.g., transmitters and receivers are collocated). In these systems, two rotating sets of transmitters/receivers may produce and receive the millimeter waves as the subject being screened is constrained to remain still inside a portal or enclosure. The images generated by such systems may have reconstruction artifacts such as dihedral effects and misrepresenting sudden indentations and protrusions due to the mono-static nature of the collected electric field data. These artifacts can lead to false alarms, which may in turn require that the subject be patted down.

Embodiments of the present systems and methods may employ the use of a plurality of synchronized or coherently-configured transmitters and receivers (e.g., sensors) positioned along an expected path of motion of a subject. The transmitters and receivers can be deployed or placed along a hallway or a conveyor belt for example. The transmitters and receivers may interrogate the subject from their placement positions relative to the unconstrained or moving subject at various time instances. The interrogation or screening may be radar-based, e.g., using millimeter wave radiation incident on and scattered from the subject. The transmitters may each transmit radiation in sequence, while the receivers spatially located around the subject measure the scattered radiation corresponding to each transmission. By using a multi-static configuration of transmitters and receivers, and combining information from the interrogations, different regions of the subject's body surface, including that of any attached foreign objects, can be reconstructed for example into a 3-dimensional or 2-dimensional outline or reconstruction estimate, without constraining the movement of the subject. A foreign object attached to the subject's body (e.g., hidden under clothing) can be detected from the reconstruction estimate, or from projection images generated from the reconstruction estimate.

Figure 2A:
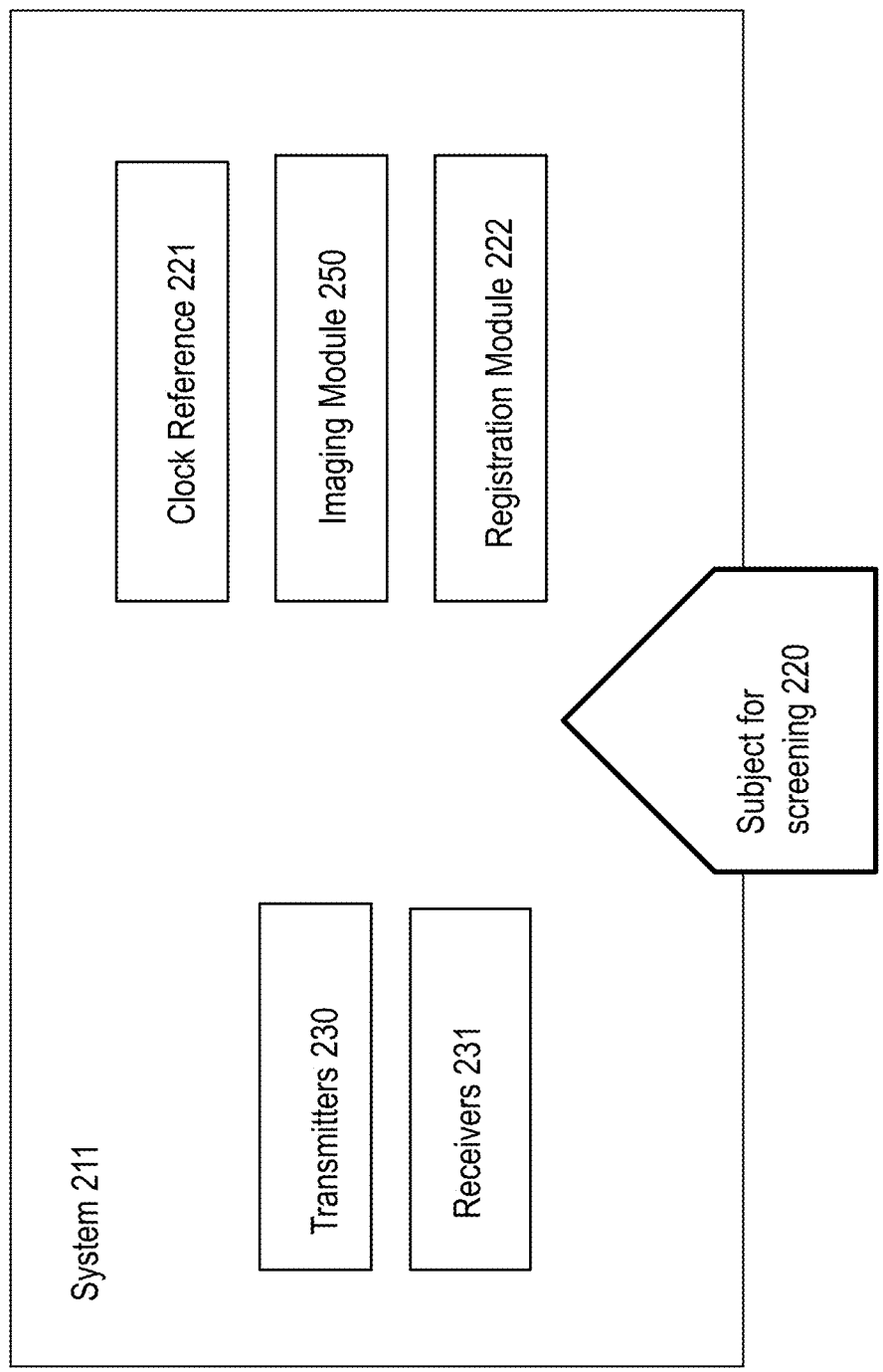
FIG. 2A is a block diagram depicting one embodiment of a system for screening an unconstrained subject.

Referring to FIG. 2A, one embodiment of a system for screening an unconstrained subject is depicted. In brief overview, the system 211 may include one or more subsystems or modules, for example, one or more transmitters 230, one or more receivers 231, an imaging module 250, a clock source 221 and/or a registration module 222. The clock source/module 221 may provide, or operate with a synchronization mechanism between the transmitters and receivers. Each of these elements, modules and/or submodules is implemented in hardware, or a combination of hardware and software. For instance, each of these elements, modules and/or submodules can optionally or potentially include one or more applications, programs, libraries, scripts, tasks, services, processes or any type and form of executable instructions executing on hardware of the device 103. The hardware may include one or more of circuitry and/or a processor, for example, as described above in connection with at least 1B and 1C. Each of the subsystems or modules may be controlled by, or incorporate a computing device, for example as described above in connection with FIGS. 1A-1C. The system 221 may sometimes be referred to as an imaging system, a radar system, a radar imaging system or a radar system for imaging.

In certain embodiments, the system 221 comprises a millimeter-wave, microwave or other radar imaging system, with the transmitters and receivers configured to operate in accordance with the respective type of system. For example, the system 221 may be implemented as an active millimeter wave system. The system may be built, designed and/or configured for screening or interrogating an unconstrained or moving subject. The system may include a plurality of synchronized transmitters and receivers placed along two or more planes, walls, surfaces or sides of a hallway, tunnel, entry way or other types of path/passage way. The transmitters and/or receivers may be placed, arranged, spaced and/or oriented so that they are expected to operate properly or optimally with respect to the expected locations and movement of the subject. Transmitters may be located around the path/passage way to provide multiple illumination angles and improved coverage. Receivers may be located around various sections of path/passage way for improved coverage and measurement of scattered radiation. In some embodiments, the receivers are placed on two panels, walls or sides of the path/passage way. This or another layout may be selected to maximize the amount of information collected, by leveraging on spatial diversity due to the multi-static configuration of the transmitters and receivers.

The spatial placements of the transmitters and/or receivers may be static, or may be adjusted or dynamically reconfigured based on operational conditions (e.g., height of a subject, the subject's speed of movement, a rerouted pathway). The transmitters may be configured to transmit or send radiation (e.g., millimeter wave) in a predetermined sequence (e.g., in the direction of an expected path of movement of the subject) or configuration. The transmitters may be configured to perform or make a series of transmissions at preconfigured intervals, or over a period of time. In some embodiments, the sequence of transmissions occur at a sufficiently high rate such that the moving subject appears to be stationary. For example, a transmitter may be configured to perform transmission of 100 microsecond in duration. Each of the transmitters may transmit in sequence, each of 100 microsecond in duration, for example. One series of transmissions over all of the transmitters may be in the order of milliseconds for example.

A series of transmissions may be repeated after a predefined time interval, e.g., when the subject is at a next location. The same transmitter can allows for reconstruction of different areas of the body surface as the subject moves through the hallway scanner. The information from the possible combinations of transmitters and/or receivers and the different positions allows for accurate reconstruction of the full body surface. As such, the present system and methods can take advantage of the subject's movement to increase the number of observation angles (e.g., from the same number of transmitters and/or receivers).

In some embodiments, the receivers are synchronized or coherently-configured to detect, measure, capture or otherwise receive radiation or fields scattered from the subject corresponding to each transmitter's transmission(s). Each receiver may comprise a sensor or detector. The configuration of transmitters and receivers may sometimes be referred to as scanners. In some embodiments, a number of receivers and/or transmitters are mounted on flat panels, which may be placed on one or more walls or sides of a hallway for example. The transmitters and their associated receivers may be spatially located such that at least one transmitter and an associated receiver are on opposite sides of the subject. The receivers and/or transmitters may inter-operate with a registration module 222 to track the locations or movement of the subject relative to each transmission and/or each reception/measurement of the scattered radiation. In some embodiments, the registration module may track the time instances and/or order of the detection/reception (e.g., relative to the locations of the subject), for processing and/or imaging each set of information detected/received corresponding to each set of scattered electric fields.

The registration module may synchronize the coherent detection/reception of scattered radiation relative to each transmission. The registration module may tap or access a clock reference 221 or clock source, and may provide or distribute the clock reference to the transmitters and/or receivers for synchronized and/or coherent operation. In some embodiments, one or more transmitters and one or more receivers may be linked with a synchronization signal based on the clock reference. The signal may comprise a very low frequency clock (e.g. 500 MHz) as compared to conventional radar systems 60 GHz. A low frequency clock may be made possible by the large up-conversion range of the system. In some embodiments, the clock source may for example comprise a frequency of 10 MHz, 100 MHz, 270 MHz, 500 MHz or other value. The clock frequency may be low, e.g., at least one or two orders of magnitude lower than an operating/center frequency of the radar system. The clock may comprise a frequency that is low enough to be transmitted or distributed via conventional and/or low-cost means, for example, via wired transmission (e.g., flexible, RF coaxial cable) or wirelessly (e.g., via GPS-based synchronization).

The clock distribution or synchronization may be performed via any wired or wireless means. The low frequency of the clock may allow one or more transmitters and/or receivers of the system to be flexibly configured. The low frequency of the clock may enable one or more transmitters and/or receivers of the system to be spatially located and/or moved into various configurations (e.g., multi-static configurations). For example, the one or more transmitters and/or receivers may be spaced far apart (e.g., on opposite sides of a large target object or region to be scanned) without affecting or substantially affecting the clock synchronization. The one or more transmitters and/or receivers may be moved, individually or with respect to one another, within any time duration, e.g., without stressing or affecting the performance of the clock synchronization means (e.g., cables). In contrast, conventional radar system uses high-frequency clocks that requires complex and expensive means (e.g., high-frequency, rigid cables) for clock synchronization/distribution.

Figure 2B:
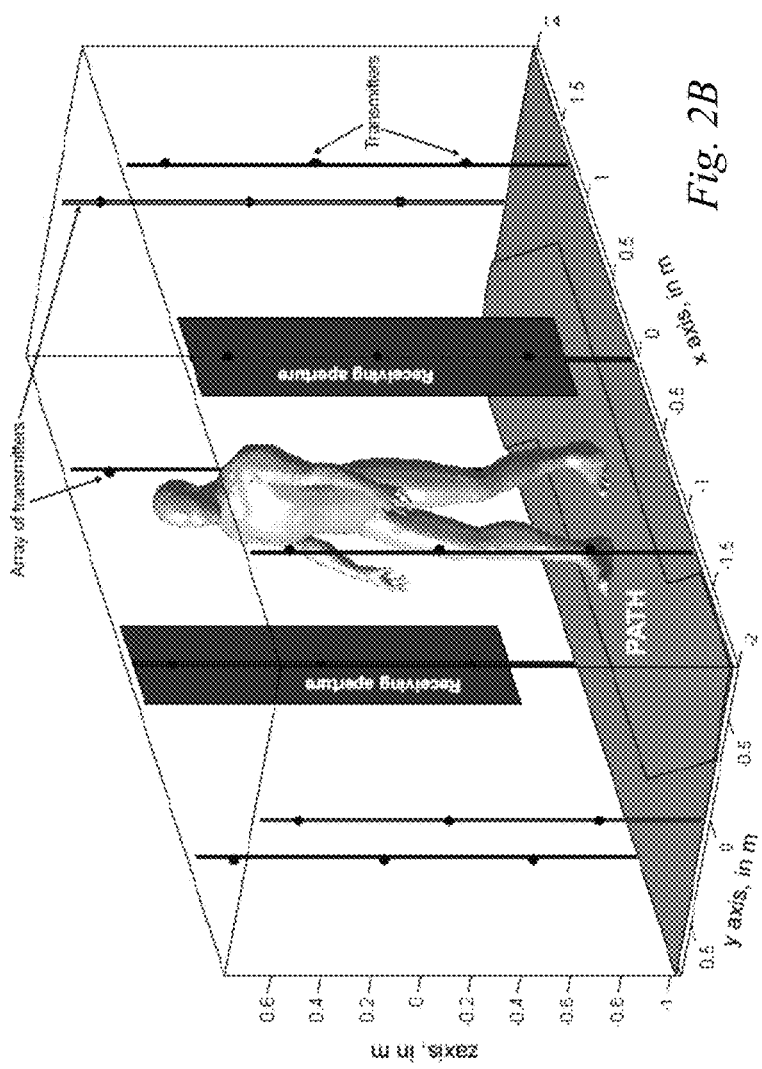
FIG. 2B depicts an illustrative representation of some embodiments of a system for screening an unconstrained subject.

In certain implementations or embodiments, the subject undergoing screening may move or be transported relative to the placements of the transmitters and receivers. FIG. 2B depicts one representation of some embodiments of a system for screening an unconstrained subject. A plurality of transmitters may be installed at certain spatial interval, for example in vertical and/or horizontal directions. The transmitters may be spaced along an expected path of movement of the subject, e.g., so as to be best placed to scan the subject from multiple angles for appropriate or optimal coverage. A plurality of receivers may reside within sections or regions sometimes referred to as receiving apertures. A multi-static arrangement of different receivers and/or receiving apertures provide increased measurement coverage for the scan.

Figure 2C:
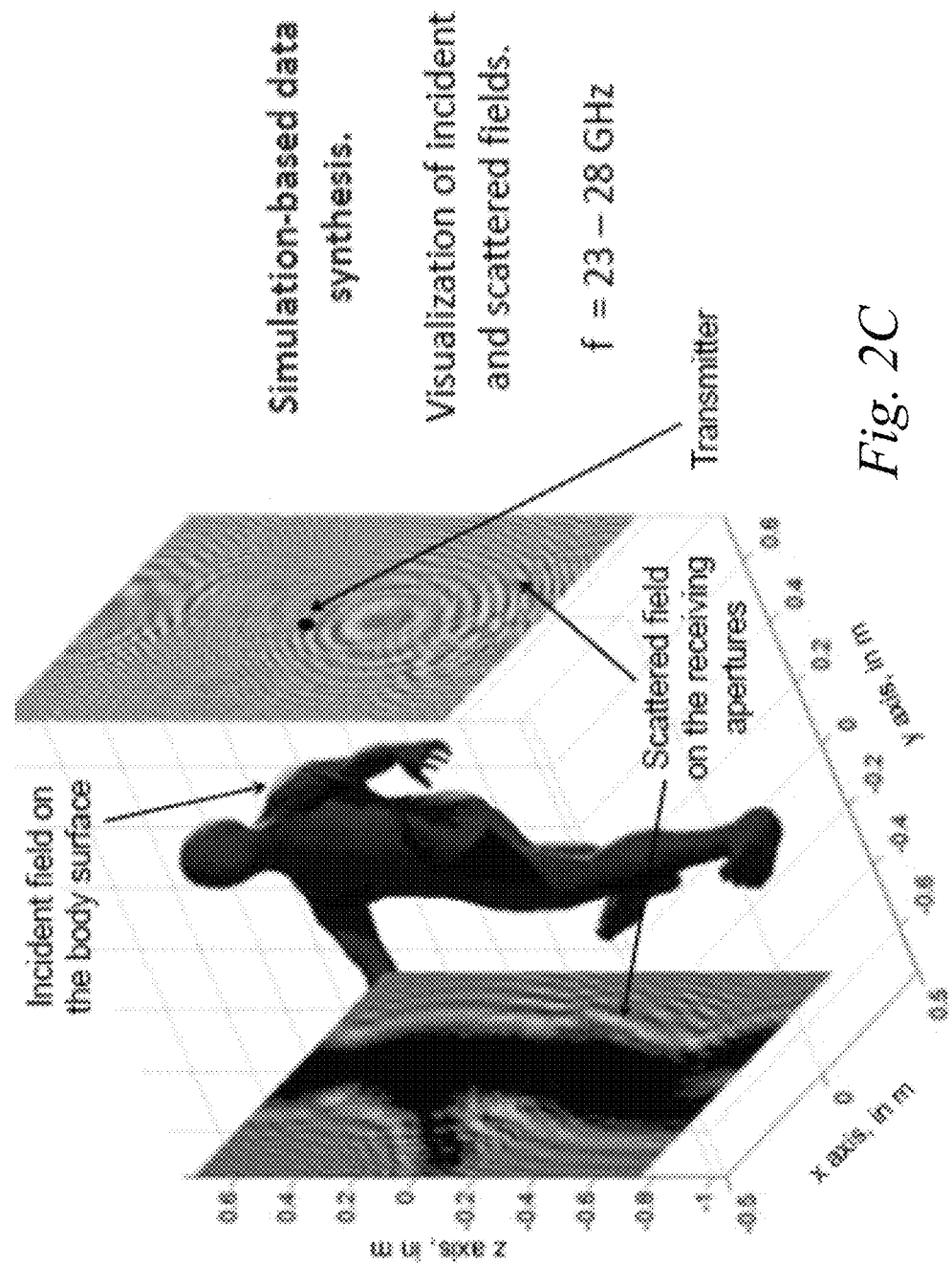
FIG. 2C depicts an illustrative representation of electromagnetic fields in connection with one embodiment of a system for screening an unconstrained subject.

Referring now to FIG. 2C, an illustrative representation of electromagnetic fields in connection with one embodiment of a system for screening an unconstrained subject is depicted. In more details, incident field transmitted from a transmitter is scattered from the body surface of the subject. An array or distribution of receivers, within receiving apertures on opposite sides of the subject (including a receiving aperture located on the other side with respect to the location of the transmitter), measures the scattered field at each of the receivers' placement locations. By way of non-limiting illustration, the operating/center frequency of the radar system may be in the range of 23 GHz to 28 GHz.

Figure 2D:
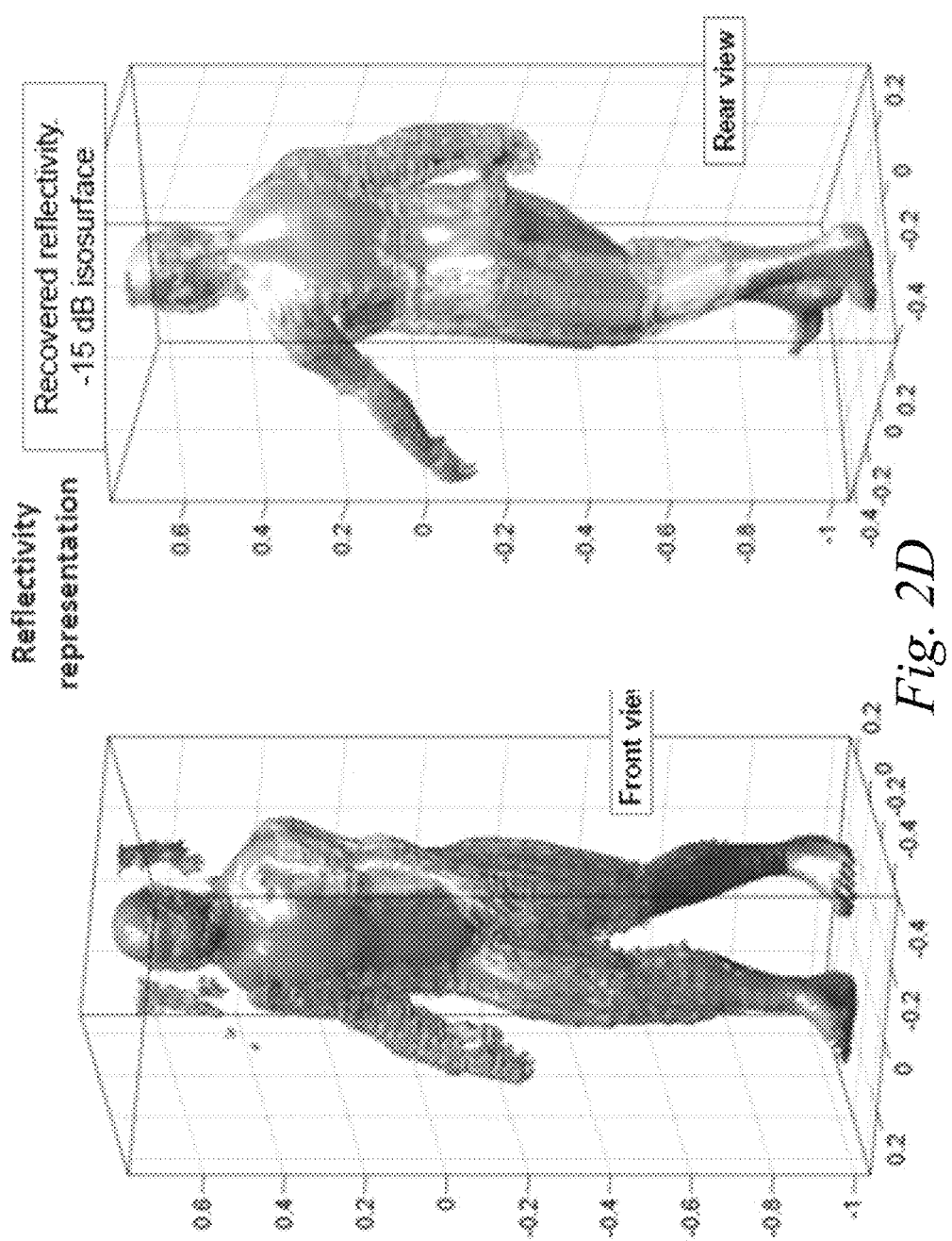
FIG. 2D depicts a reflectivity representation of a body surface in multiple views based on one embodiment of a method for screening an unconstrained subject.

Referring again to FIG. 2A, the system may include an imaging module 250. The imaging module may process measurements by the receivers of the scattered radiation. The imaging module may perform backpropagation of the scattered field. The imaging module may be configured, designed and/or implemented to perform Fourier-based multi-static radar imaging. The imaging module may generate or otherwise produce one or more partial outlines or reconstruction estimates of a body surface of the subject and any attached foreign object. FIG. 2D depicts a reflectivity representation of a body surface in multiple views based on one embodiment of a method for screening of an unconstrained subject. The reconstruction estimate, indicated by textured surfaces, may represent portions of the body surface generated from the scattered fields. The incomplete or partial reconstruction estimate may reflect partial or insufficient coverage offered by a limited number of transmitters (e.g., one transmitter) and a limited number of receivers (e.g., within two receiving apertures). The imaging module may generate a reconstruction estimate based on, or up to a predetermined threshold, e.g., a recovered reflectivity of −15 dB or other value. Both front and rear views of the reflectivity representation are illustrated in FIG. 2D.

Figure 2E:
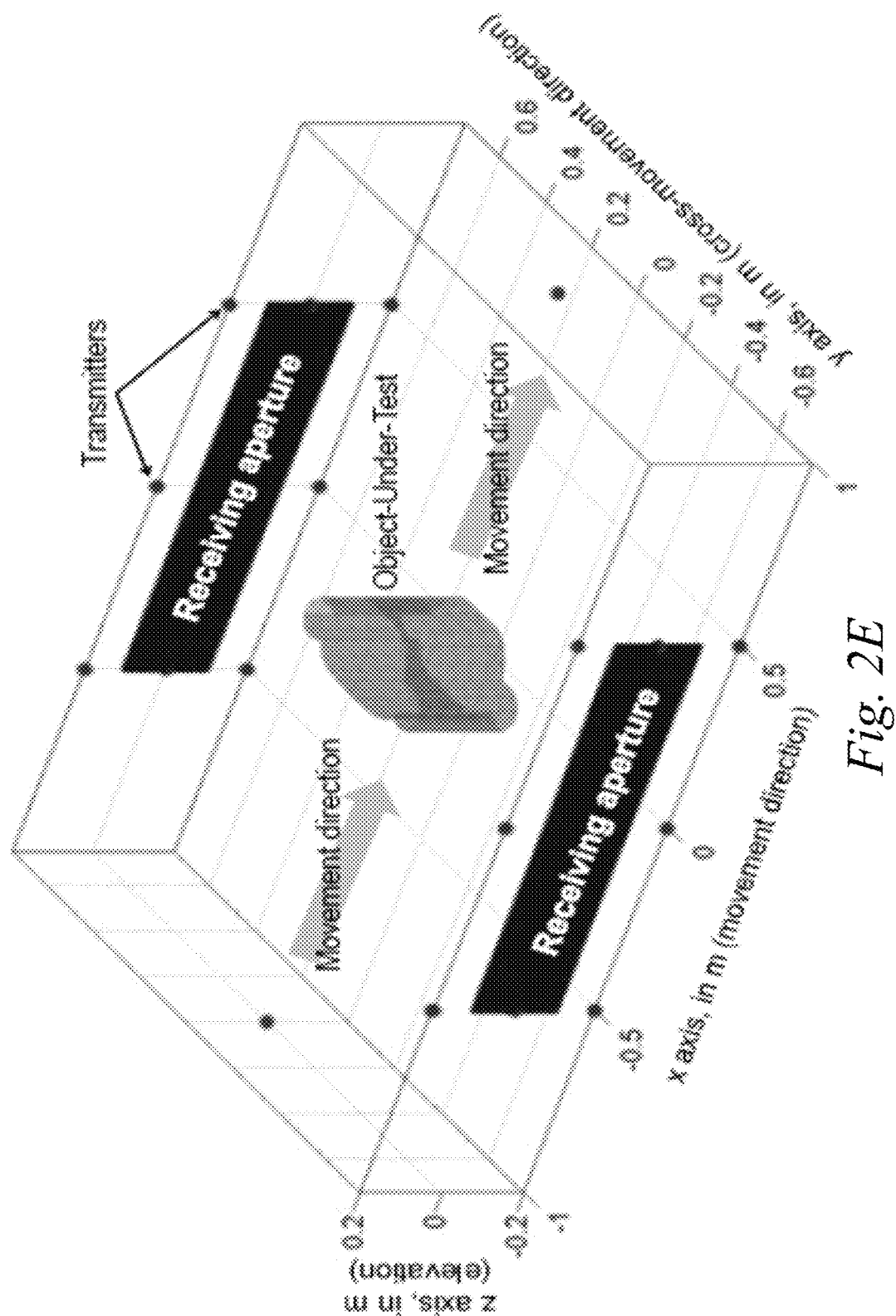
FIG. 2E depicts another representation of some embodiments of a system for screening an unconstrained subject.
Figure 2F:
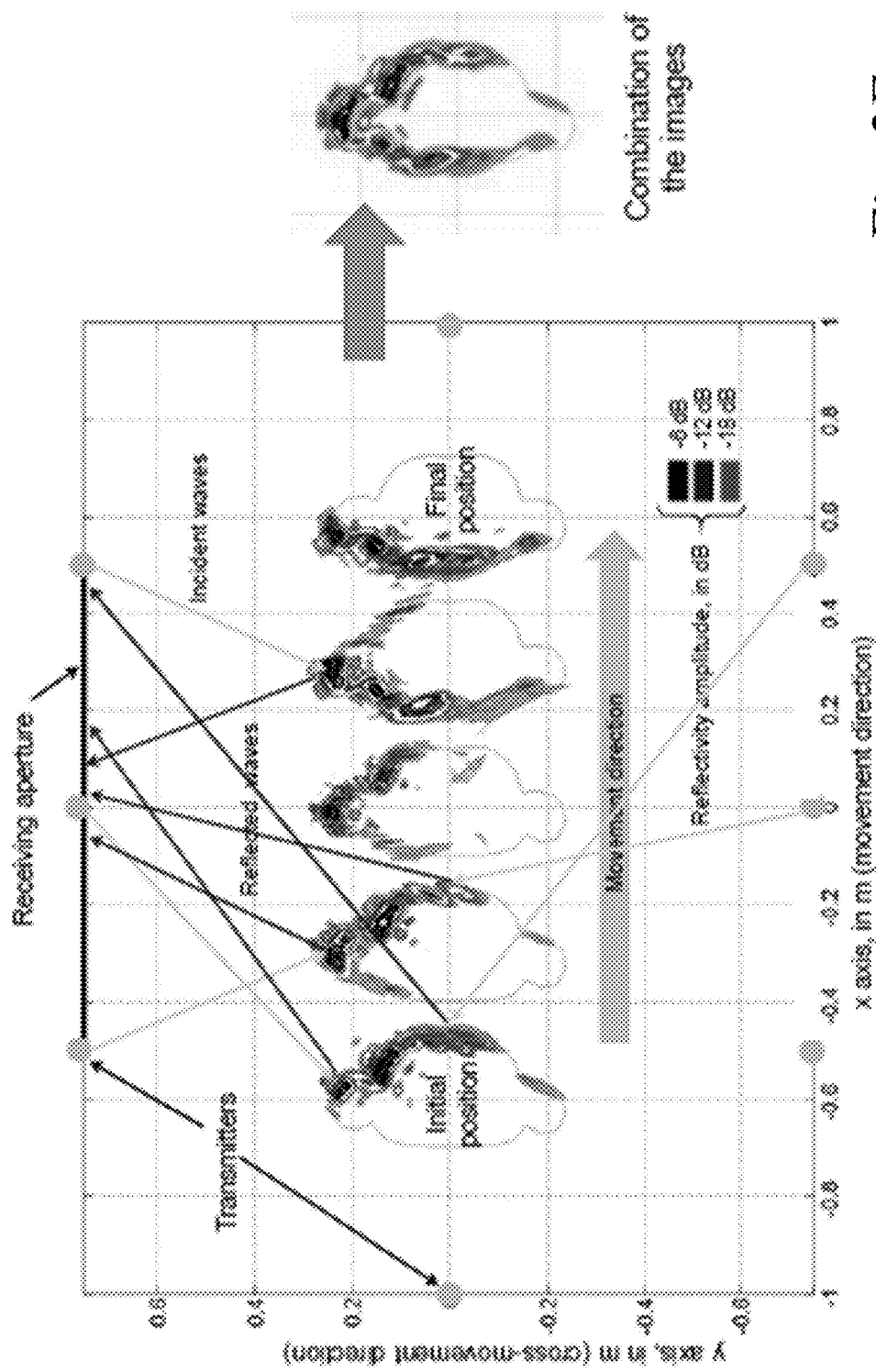
FIG. 2F depicts imaging results based on one configuration of some embodiments of a system for screening an unconstrained subject.

By way of illustration, FIG. 2E depicts another representation of some embodiments of a system for screening an unconstrained subject. The subject, which may comprise an object of interest or an object under test, can move in a certain direction between a spatial distribution of transmitters and receivers. FIG. 2F depicts imaging results based on one configuration of some embodiments of a system for screening an unconstrained subject. In more details, this configuration includes one receiving aperture of receivers, and transmitters located on at least two sides of the subject. The subject is scanned at a plurality of locations or time instances, by the plurality of transmitters. In certain embodiments, one or more transmitters may be placed in front of, and/or to the rear of the subject. In some embodiments, each radiation source or transmitter may approximately represent an omnidirectional or "multi-directional" transmitter (e.g., due to the limited size of the radiation source).

The transmitted fields are reflected or scattered from different regions of the subject's body surface, similar to reflections off a mirror-ball. Some of the reflected waves are directed towards some of the receivers' locations (e.g., within the receiving apertures) and are measured. For simplicity and/or clarity of illustration, FIG. 2F depicts imaging results for one receiving aperture. Different reflectivity amplitudes are indicated in the images generated by the imaging module for each location of the object. For example, the imaging module may perform the imaging as the subject continuously moves through the hallway scanner, and combine the recovered image for every position (e.g., as different frames of a video).

The imaging module can combine or overlay the different images to generate a more complete reconstruction estimate of the body surface. The imaging results illustrates that different portions of the subject may be imaged or emphasized by the same configuration of transmitters and/or receivers. Therefore, an entire or a more complete surface of the subject may be recovered or reconstructed when combining images retrieved for different positions along the subject's path of movement.

In some embodiments, the imaging module may generate projections of the reconstruction estimate or image values onto one or more planes (or imaging directions). The depth information may be lost and there may be notable missing regions of the image for a given imaging direction, but the resulting image set may be easier for visual inspection, e.g., by a person. The imaging module may generate one or more projections from the 3-dimensional surface outlines or reconstruction estimate, e.g., to support data visualization. The one or more projections may each comprise a 2-dimensional image, e.g., of a certain viewing direction relative to the 3-dimensional surface outline. In some embodiments, the imaging module may collapse or remove the depth information along a particular viewing or imaging direction to generate a projection. In certain embodiments, the imaging module may remove or result in loss of image features, e.g., those features occluded or hidden by other overlaying features.

Embodiments of the present systems and methods can provide full body coverage for imaging without interrupting forward steady pedestrian movement, for example. The present systems and methods can be used to perform imaging for high throughput, non-invasive, minimal disruption scanning. Non-obtrusive scanning is possible with embodiments of the present systems and methods. In some embodiments, the present systems and methods can allow higher probability of detection of foreign attached objects, and lower false alarm rate due to the use of multiple observation angles in a multi-static configuration.

Figure 2G:
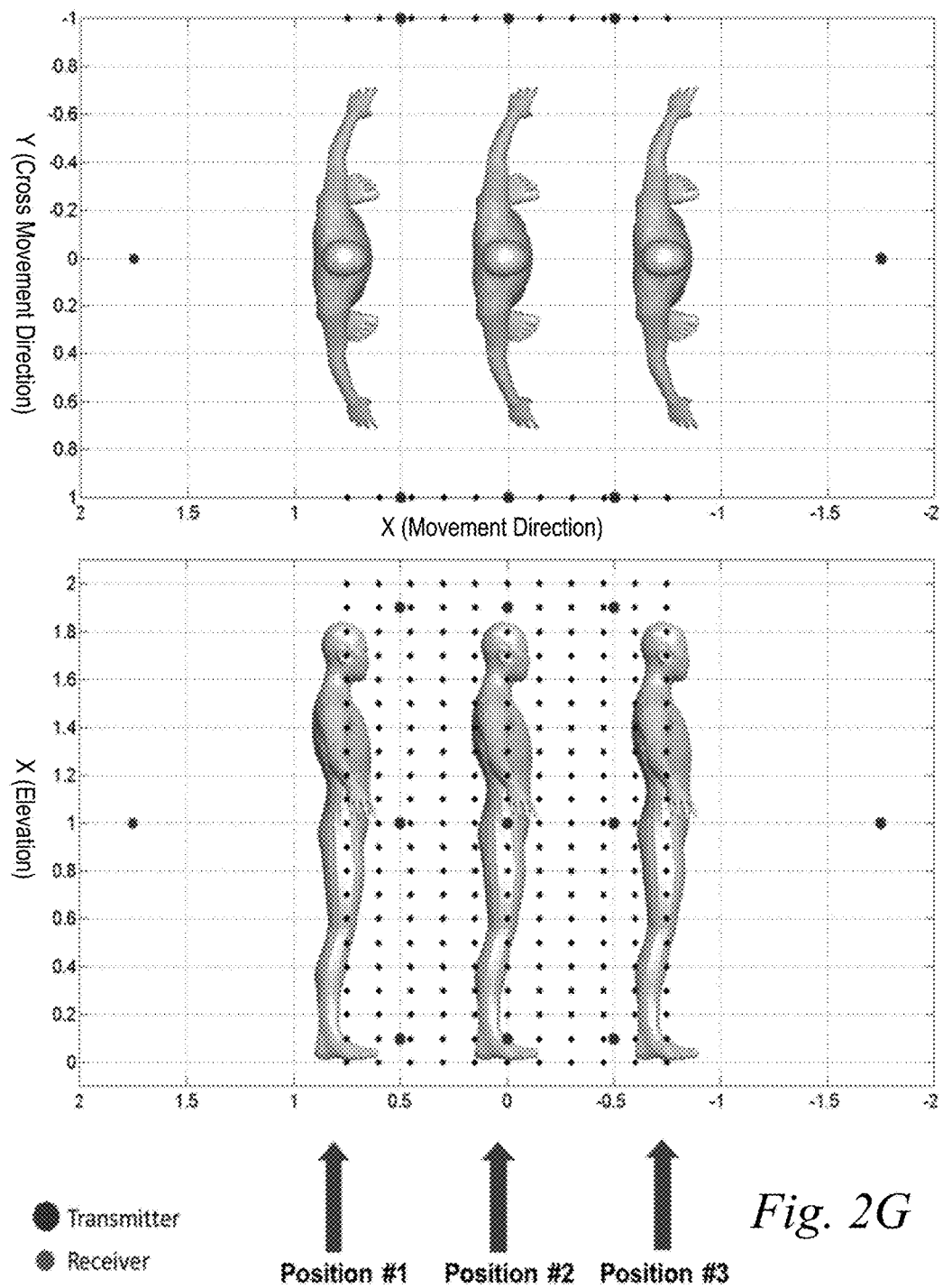
FIG. 2G depicts a representation of some embodiments of a system for screening an unconstrained subject.

Referring now to FIG. 2G, a representation of some embodiments of a system for screening an unconstrained subject is depicted. In more details, a layout of the system is shown, in top view and in side view relative to a subject. The subject undergoing screening is scanned at different positions as the subject moves or walks between a spatial arrangement of transmitters and receivers, sometimes referred to as a hallway scanner. By way of illustration, a two-dimensional array of transmitters and receivers may be configured, spanning at least the height of the subject. In some embodiments, additional transmitters in front of and/or behind the subject can also be used to ensure information from all possible angles is collected. In certain embodiments, transmitters and/or receivers may be placed above, below, or otherwise around the unconstrained subject or the subject's path of movement.

As the subject moves within the hallway scanners, the transmitters may be sequentially activated and the electric field, which is then scattered by the person, may be collected by all the receivers at the same time. In some embodiments of the system, fast electronic switching allows for the quick activation of the plurality of transmitters in sequence and the corresponding data collection by the receivers. In this way, information from multiple relative positions of the subject from the scanner can be collected, stored and/or processed.

Referring now to FIG. 2H, one embodiment of a system for screening an unconstrained subject is depicted. For a top view, the propagation directions of incident and scattered millimeter waves are depicted when the subject is in two different locations relative to the same active transmitter. The same transmitter allows for reconstruction of different areas of the body as the subject walks through the scanner and assumes different positions relative to the transmitter. The different areas of the body are measured using different receivers due to changes in the propagation directions of the incident and scattered millimeter waves when the subject assumes different positions. FIG. 2I depicts an embodiment of a system for screening an unconstrained subject. Similar to FIG. 2H, the top view representation in FIG. 2I shows that a single transmitter (e.g., located in front of the subject) can result in different propagation directions of incident and scattered waves when the subject is in two different locations relative to the same active transmitter, and different portions of the body can be measured using different receivers due to changes in the propagation directions.

Between FIGS. 2H and 2I, when the subject is at the same location, different active transmitters (sequentially making transmissions) can result in different propagation directions of incident and scattered waves. Therefore, different portions of the body can be measured using different receivers due to changes in the propagation directions. Different areas on the body contour can be primarily reconstructed when using each transmitter. Accordingly, the combination of the information measured from different possible combinations of transmitters/receivers, as well as the different positions of the subject relative to transmitters/receivers can allow for accurate reconstruction of the full body surface. One aspect of some embodiments of the present systems and methods is that for every transmitter, all or some of the receivers on both sides of the subject should receive the scattered waves, not just those receivers adjacent to a given transmitter.

In some embodiments, the imaging module executes an imaging algorithm to produce an image from the scattered radiation. For instance, and in some embodiments, a fast implementation of a multi-static Synthetic Aperture Radar (SAR) technique may be used to create images proportional to the reflectivity of the body under test or undergoing screening. In certain embodiments, multiple frequencies may be transmitted and may be received on both walls or sides of the sensors. Given the total electric field at receiver r when the transmitter t is active at frequency l, $E_{r,t}^l$ the SAR image at a pixel placed at a point $\vec{r}'$ is generated as:

$$I_r(\vec{r}') = \sum_{l}^{Nfreq} E_{r,t}^l e^{+jk_l|\vec{r}_t - \vec{r}'|} e^{+jk_l|\vec{r}_r - \vec{r}'|} \quad (1)$$

where $N_{freq}$ may be the total number of used frequencies, $k_l$ is may be the wavenumber at frequency l and $\vec{r}_r$ and $\vec{r}_r$ may be the positions of the transmitter and receiver respectively. The total image for one pixel in the observation domain may be calculated using the total number of receivers $N_{rx}$ as:

$$I_r(\vec{r}') = \sum_{r}^{Nrx} I_r(\vec{r}') \quad (2)$$

In some embodiments of the present systems and methods, Fast Fourier Transform (FFT) techniques can be effectively used to accelerate the reconstruction and achieve real time images. The reconstruction domain may be slowly displaced to always enclose the subject undergoing screening. Registration of the subject's position can be done using the radar itself (e.g., via the registration module) and may be improved with video cameras or other suitable sensors. This can allow tracking of the subject's movements during the scanning time regardless of his motion inside the system. In some embodiments, the final image is obtained by combining (e.g., in magnitude) the images obtained from the subject in the different captured positions inside the hallway scanner.

By way of illustration, and not intended to be limiting in any way, a two dimensional reconstruction setup may include two lines of transmitters and receivers. The setup for the illustrative system may include the configuration described in Table I. The system layout may be same one presented in FIGS. 2H and 2I for example. In order to easily combine all the images, it may be assumed that the Subject remains in the same posture as the Subject walks through the hallway Scanner, so that overlapping portions of the generated partial reconstruction estimates can be aligned and combined over the multiple images. The system can incorporate various advanced methods to combine the set of images, compensate for the Subject's motion, and/or address the subject's changes in posture.

TABLE 1 example parameters

| | |
|---|---|
| Range of frequencies | 23-28 GHz |
| Number of transmitters | 12 |
| Number of receivers | 64 |
| Intermediate positions (# of acquired images) | 11 |

Figure 2J:
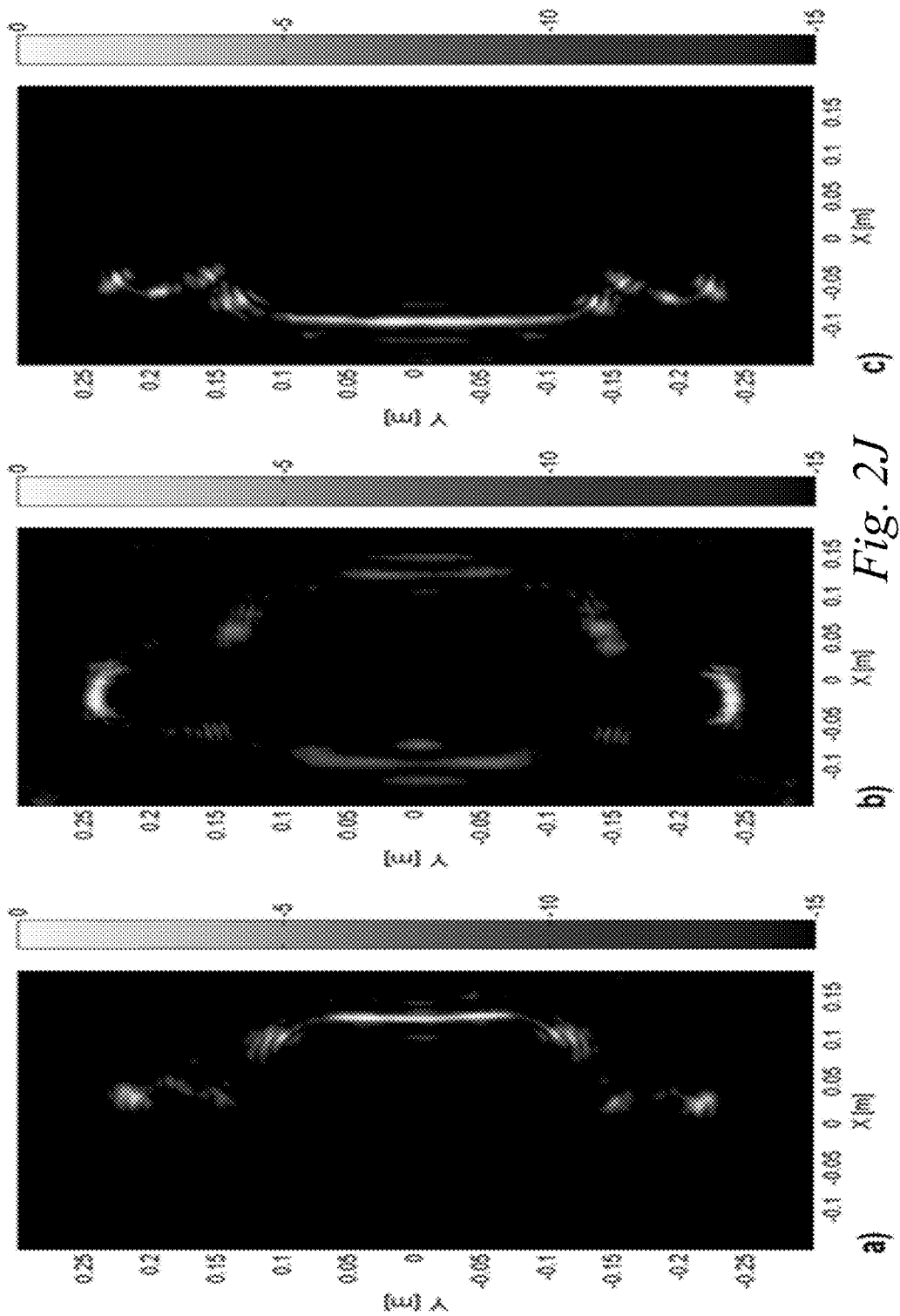
FIG. 2J depicts images or partial reconstruction estimates obtained for different positions of a subject.
Figure 2K:
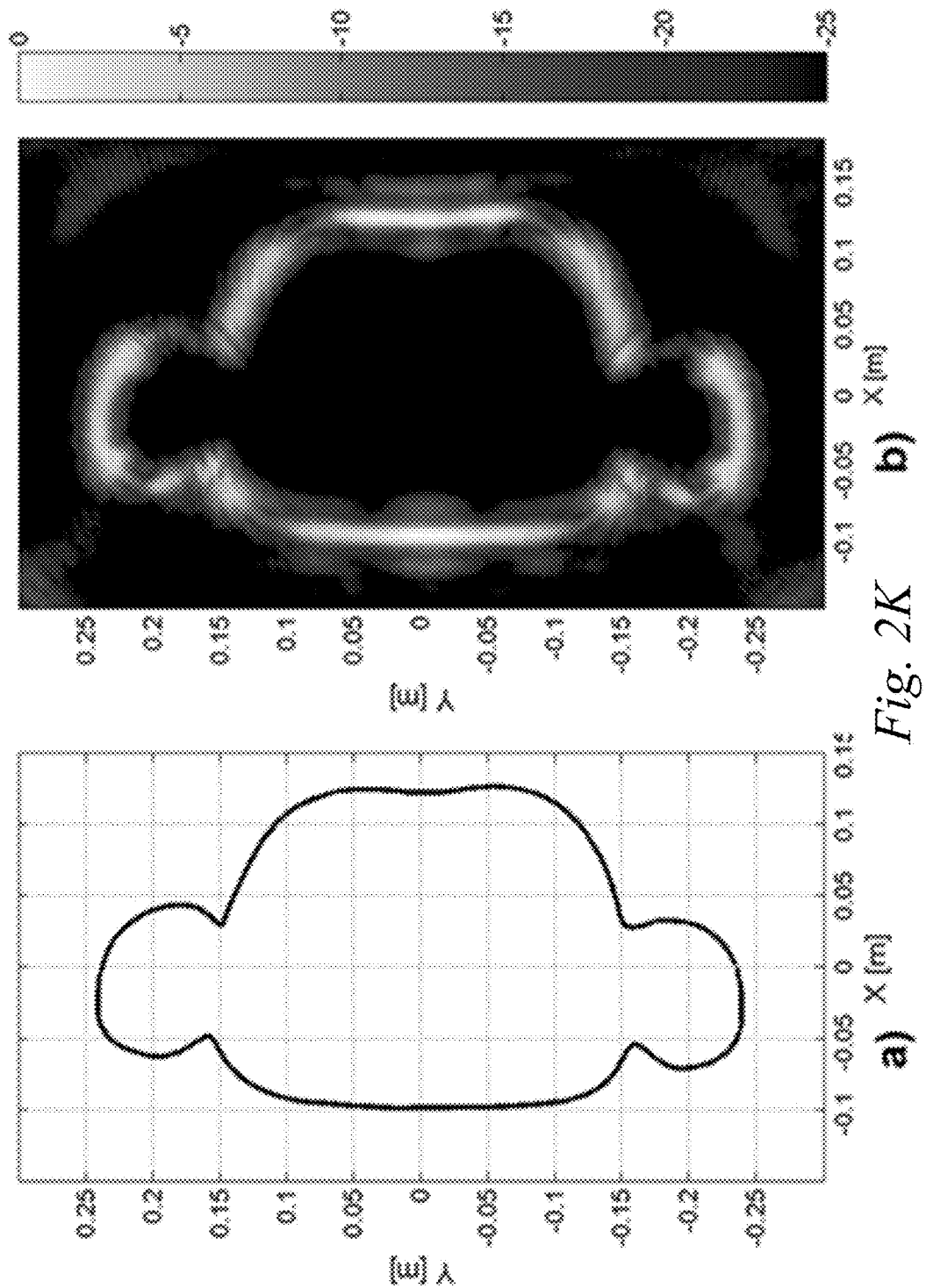
FIGS. 2K and 2L depict reconstruction estimates obtained from embodiments of a system for screening an unconstrained subject.
Figure 2L:
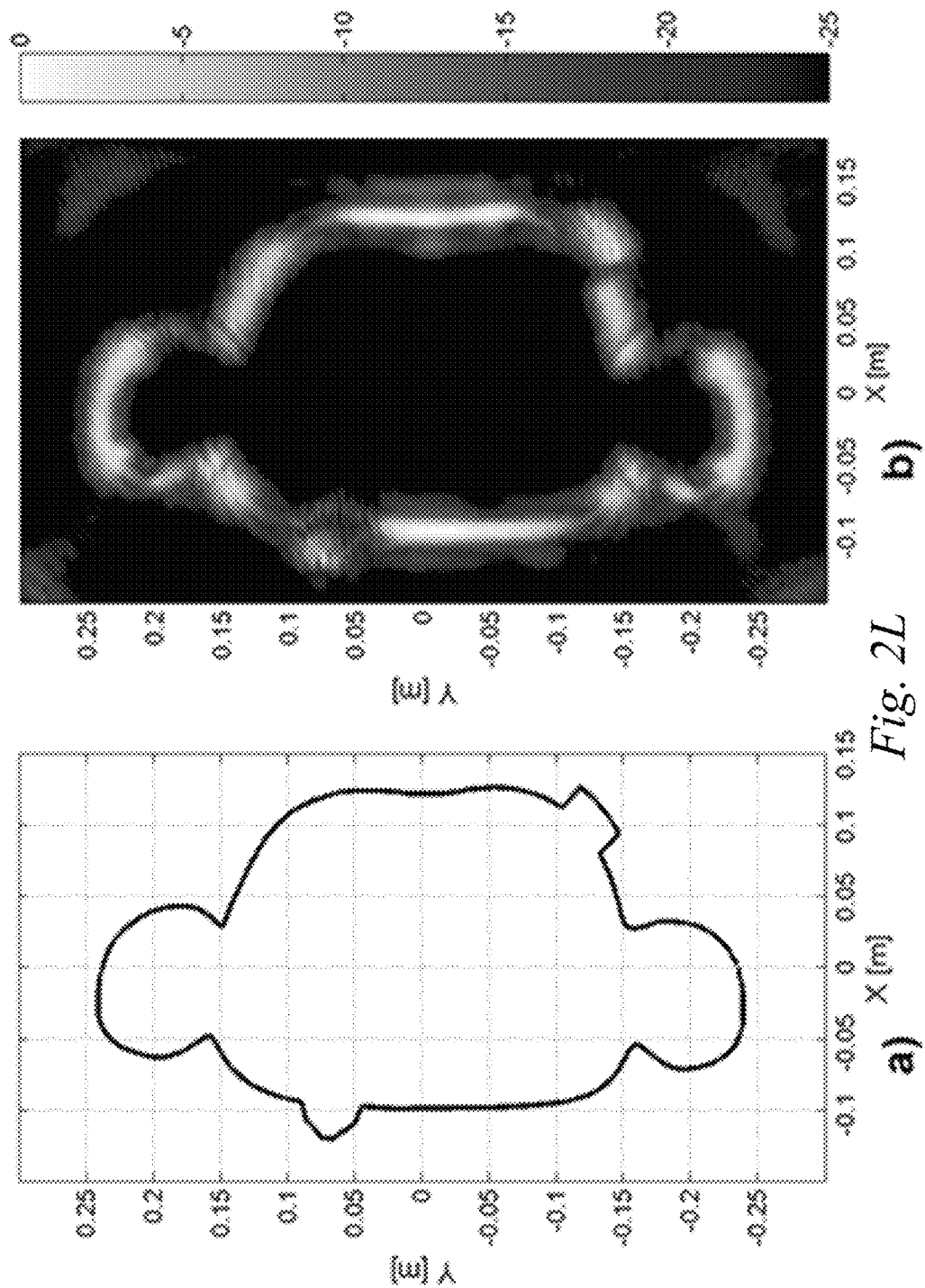

FIG. 2J shows images or partial reconstruction estimates obtained using the 12 transmitters and 64 receivers for three different positions of the Subject. The positions of the Subject may correspond to the three positions depicted in FIG. 2G, for example. Different areas of the Subject's body may be reconstructed depending on the subjects position inside the hallway scanner. The partial reconstruction estimates may comprise reflectivity images generated at each position. A reconstructed image, comprising a coherent combination of the images (e.g., assuming the same exact contour for a number of intermediate positions) is illustratively shown in part (b) of FIG. 2K together with the ground truth (or actual contour, in part (a)) for comparison purposes. Similar results for the same contour with two added small objects are presented in FIG. 2L to indicate the ability of the system to identify foreign objects attached to the body. Embodiments of the system may incorporate and use Automatic Threat Recognition (ATR) with the images to ensure privacy of the subject.

By way of illustration, a three dimensional reconstruction example using a target object with no variation in elevation that resembles a human torso, is depicted in FIG. 2M. A suitable system layout that can used in this reconstruction example is referenced in FIG. 2E. For instance, five intermediate positions (from −80 to +80 cm) may be scanned. Two receiving panels of 1 m×0.2 m with receivers placed every 0.5 wavelengths may be implemented. As illustratively shown in depicted in FIG. 2E, twenty transmitters may be used to provide multiple illumination angles. The combination of the reflectivity, showing good agreement with the ground truth, is shown in FIG. 2M. In particular, part (a) depicts the reconstructed normalized reflectivity obtained using the example system, with a −12 and −18 dB isosurface, and part (b) depicts the reconstructed normalized reflectivity with a −12 dB isosurface.

Figure 2N:
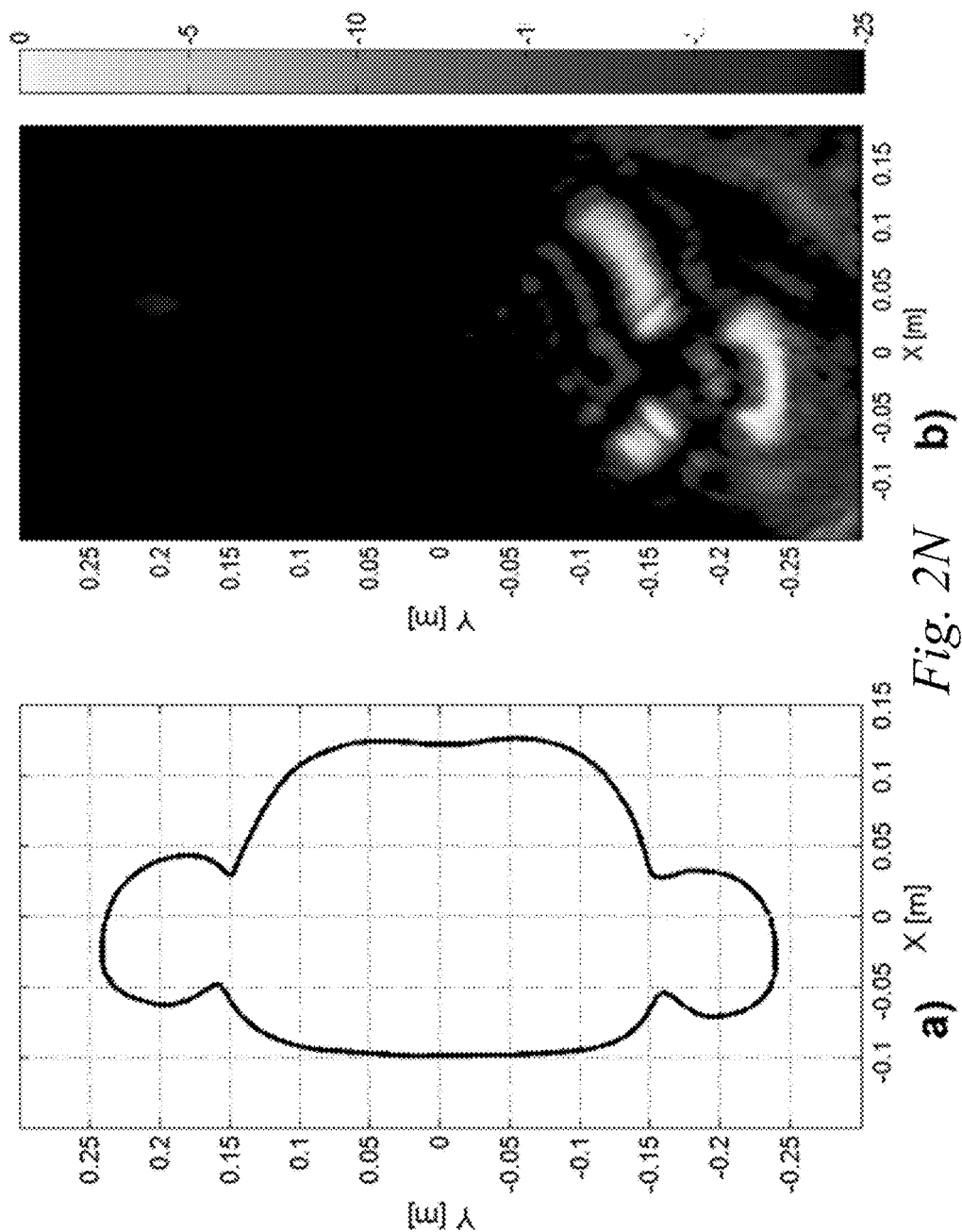
FIG. 2N depicts an example of a reconstruction estimate obtained based on one wall or side of transmitters and receivers.
Figure 20:
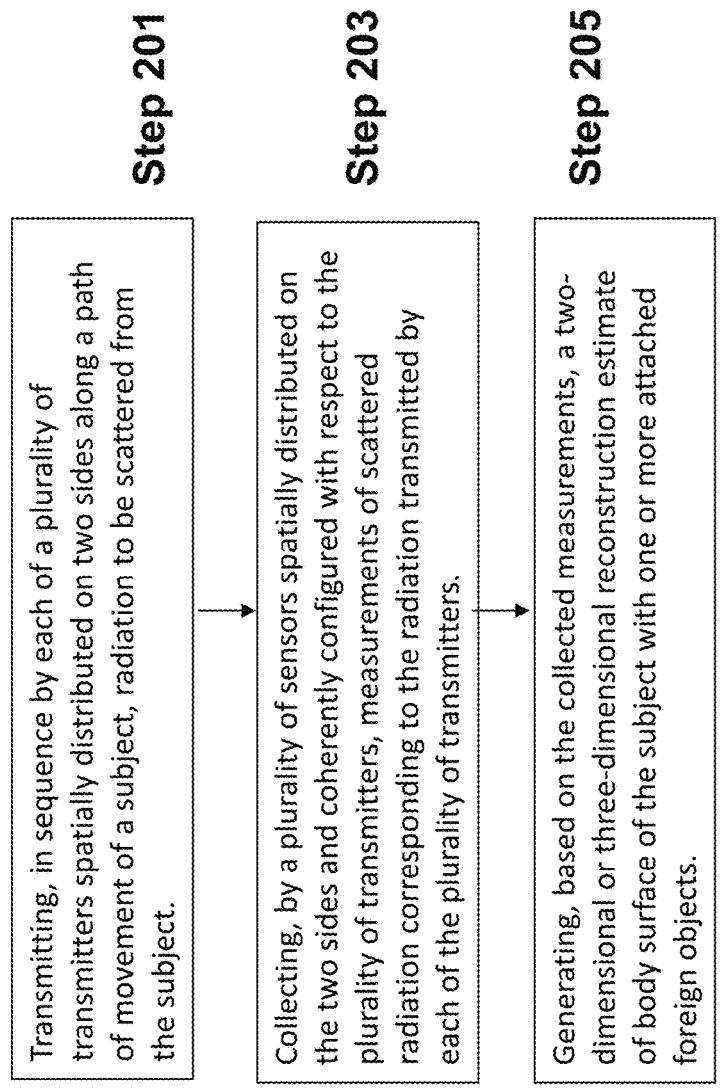

In some implementations, transmitters and receivers are placed in the same side of the Subject (e.g., due to limitations in distributing a reference clock to the transmitters and receiver). FIG. 2N illustratively shows an image that would be obtained using only one wall or side of transmitters and receivers. Similarly, a reconstructed image, comprising a coherent combination of the images is illustratively shown in part (b) of FIG. 2N together with the actual contour, in part (a), for comparison purposes. The image in (b) indicates that coverage may be significantly reduced so that a smaller portion reconstructed image may also be lower than that from an implementation with two walls of transmitters and/or receivers. Single-sided multi-static radar systems, as well as mono-static radar systems, may not be able to image, for example, the front of the torso of a Subject walking past a sensing wall. To image the entire body Surface, receivers on two walls can be used to receive the scattered waves for every transmitter. As can be observed, the coherent combination of two (or more) walls of transmitters and/or receivers can significant improve on, and overcome most of the limitations of the single-wall/side implementation. In some embodiments, the use of two walls/sides of transmitters and/or receivers is also more cost-effective and/or easier to deploy than four walls/sides of single-sided multi-static panels of sensors. In the latter, some areas of the body surface would be still invisible or unreachable due to the lack of coherence between the independent panels of sensors.

Referring now to FIG. 2O, one embodiment of a method for screening an unconstrained subject is depicted. Each of a plurality of transmitters spatially distributed on two sides along a path of movement of a subject may transmit, in sequence, radiation to be scattered from the subject (201). A plurality of sensors may collect measurements of scattered radiation corresponding to the radiation transmitted by each of the plurality of transmitters (203). The plurality of sensors may be spatially distributed on the two sides and coherently configured with respect to the plurality of transmitters. An imaging module may generate, based on the collected measurements, a two-dimensional or three-dimensional reconstruction estimate of body surface of the subject with one or more attached foreign objects (205).

Referring now to (201), and in some embodiments, each of a plurality of transmitters spatially distributed on two sides along a path of movement of a subject may transmit, in sequence, radiation to be scattered from the subject. The plurality of transmitters may be spatially distributed on one or more sides along the path of movement. One each side, the transmitters may be spatially distributed as a string, line, row, column and/or array (e.g., 1D, 2D or 3D array) of transmitters. The plurality of transmitters may be spatially distributed along an expected path of motion of a subject. Each transmitter may illuminate the subject from the transmitter's placed location.

The transmitters may each illuminate or provide incident radiation to the subject from their respective placement positions relative to the unconstrained or moving subject at different time instances. For example and in some embodiments, a first transmitter located on a first side of the two sides along the path of movement may transmit radiation at a first time instance. A second transmitter located on a second side of the two sides along the path of movement may transmit radiation at a second time instance. A third transmitter located on the first or second side may transmit radiation at a third time instance, and so on. The transmitters may each transmit radiation in sequence, e.g., with no overlapping transmissions. The transmitters may perform or make a series of transmissions at preconfigured intervals, or over a period of time. In some embodiments, the sequence of transmissions occur at a sufficiently high rate such that the moving subject appears to be stationary. When the subject is at a certain location, different active transmitters (sequentially making transmissions) can result in different propagation directions of incident and scattered waves. A series of transmissions may be repeated after a predefined time interval, e.g., when the subject is at a next location.

Referring now to (203), and in some embodiments, a plurality of sensors may collect measurements of scattered radiation corresponding to the radiation transmitted by each of the plurality of transmitters. Incident field or radiation transmitted from a transmitter is scattered from the body surface of the subject. Some of the reflected waves are directed towards some of the sensors' locations. The plurality of sensors may be spatially distributed on the two sides and coherently configured with respect to the plurality of transmitters. The receivers may be configured to operate in a multi-static configuration with respect to each of the transmitters.

The receivers and/or transmitters may communicate with, or be controlled by a registration module to track the locations and/or movement of the subject relative to each transmission and/or each measurement of the scattered radiation. The registration module may track the time instances and/or order of the measurements, for processing and/or imaging each set of information collected corresponding to each set of scattered electric fields. The registration module may synchronize the coherent detection/reception of scattered radiation relative to each transmission. The registration module may tap or access a clock reference 221 or clock source, and may provide or distribute the clock reference to the transmitters and/or receivers for synchronized and/or coherent operation.

In some embodiments, all or some receivers (sensors) may concurrently or simultaneously collect or take measurements of scattered fields corresponding to a transmitter's transmission. For example, a first sensor located on a first side of the two sides along the path of movement may collect, at a first time instance, a measurement of a first scattered radiation corresponding to radiation transmitted by a first transmitter of the plurality of transmitters. A second sensor located on a second side of the two sides along the path of movement may collect, at the same first time instance, a measurement of a second scattered radiation corresponding to radiation transmitted by the first transmitter. A third sensor located on either the first or second side of the two sides may collect, at the same first time instance, a measurement of a third scattered radiation corresponding to radiation transmitted by the first transmitter.

The receivers may be synchronized or coherently-configured to detect, measure, capture or otherwise receive radiation or fields scattered from the subject corresponding to each transmitter's transmission(s). The transmitters may each transmit radiation in sequence, while the receivers spatially located around the subject can measure the scattered radiation corresponding to each transmission. For example, the plurality of sensors may collect measurements of radiation scattered from the subject at a first position along the path of movement based on radiation from a first transmitter of the plurality of transmitters, and measurements of radiation scattered from the subject at a second position along the path of movement based on radiation from a second transmitter of the plurality of transmitters. The two sets of measurements may be collected at the times corresponding to the two transmissions. Different areas of the subject's body may be measured using different receivers due to changes in the propagation directions of the incident and scattered waves when the subject assumes different positions. Accordingly, the combination of the information measured from different possible combinations of transmitters/receivers, as well as the different positions of the subject relative to transmitters/receivers can allow for accurate reconstruction of the full body surface.

The transmitters and their associated receivers may be spatially located such that at least one transmitter and an associated receiver are on opposite sides of the subject. In some scenarios or implementations, a first sensor collects a measurement of radiation scattered from the subject based on radiation transmitted by a first transmitter. The first transmitter and the first sensor may have a subtended angle of at least 90 degrees relative to the subject. In some scenarios or implementations, the same sensor may collect a measurement of radiation scattered from the subject based on radiation transmitted by a (e.g., another) transmitter, the transmitter and the sensor having a subtended angle less than 90 degrees relative to the subject.

In some embodiments, a transmitter is located in front of the subject or behind the subject along the path of movement. The transmitter may transmit, at a first time instance, radiation incident on the subject. The plurality of sensors may collect measurements of radiation scattered from the subject corresponding to the radiation transmitted by the first transmitter. The plurality of sensors may collect measurements of radiation scattered from the subject corresponding to a second transmission from the first transmitter when the subject is at a another location. One or more front and/or rear transmitters may provide additional diversity for angles of illumination and scattering angles.

Referring now to (205), and in some embodiments, an imaging module may generate, based on the collected measurements, a two-dimensional or three-dimensional reconstruction estimate of body surface of the subject with one or more attached foreign objects. The imaging module may process measurements by the receivers of the scattered radiation. The imaging module may generate a two-dimensional or three-dimensional outline of the subject based on the collected measurements. The imaging module may perform backpropagation of the scattered field. The imaging module may perform Fourier-based multi-static radar imaging. The imaging module may execute a multi-static SAR technique to create images proportional to the reflectivity of the body under test or undergoing screening. The imaging module may use FFT techniques to accelerate the reconstruction and achieve real time images.

The imaging module may generate or otherwise produce one or more partial reconstruction estimates or partial outlines of the body surface of the subject (and any foreign attached objects). Each of the plurality of partial reconstruction estimates may be generated based on measurements of scattered radiation corresponding to radiation transmitted by a respective transmitter from the plurality of transmitters. The imaging module may perform imaging as the subject continuously moves through the hallway scanner, and combine the recovered image or reconstruction estimate for every position. The imaging module can combine or overlay the different images to generate a more complete reconstruction estimate of the body surface.

A registration module may track or register a position of the subject along the path of movement with a corresponding one of the plurality of partial reconstruction estimates. For example, the registration module may track the subject's position using the radar itself and/or using video cameras or other suitable sensors. The imaging module may combine the plurality of partial reconstruction estimates to generate the two-dimensional or three-dimensional reconstruction estimate. The imaging module may generate a reconstruction estimate based on reflectivity values. The imaging module may generate a reconstruction estimate based on, or up to a predetermined threshold, e.g., a recovered reflectivity of −15 dB or other value.

The imaging module may generate a final image combining (e.g., in magnitude) the images obtained from the subject in the different captured positions. By using a multi-static configuration of transmitters and receivers, and combining information from the interrogations, different regions of the subject's body surface, including that of any attached foreign objects, can be reconstructed into a 3-dimensional or 2-dimensional outline or reconstruction estimate, without constraining the movement of the subject. A foreign object attached to the subject's body (e.g., hidden under clothing) can be detected from the reconstruction estimate, or from projection images generated from the reconstruction estimate.

In some embodiments, the imaging module may generate projections of the reconstruction estimate or image values onto one or more planes (or imaging directions). The imaging module may generate one or more projections from the 3-dimensional surface outlines or reconstruction estimate, e.g., to support data visualization. The one or more projections may each comprise a 2-dimensional image, e.g., of a certain viewing direction relative to the 3-dimensional surface outline. In some embodiments, the imaging module may collapse or remove the depth information along a particular viewing or imaging direction to generate a projection. In certain embodiments, the imaging module may remove or result in loss of image features, e.g., those features occluded or hidden by other overlaying features.

It should be noted that certain passages of this disclosure can reference terms such as "first" and "second" in connection with receivers, transmitters, etc., for purposes of identifying or differentiating one from another or from others. These terms are not intended to merely relate entities (e.g., a first receiver and a receiver sensor) temporally or according to a sequence, although in some cases, these entities can include such a relationship. Nor do these terms limit the number of possible entities (e.g., receivers) that can operate within a system or environment.

It should be understood that the systems described above may provide multiple ones of any or each of those components and these components may be provided on either a standalone machine or, in some embodiments, on multiple machines in a distributed system. In addition, the systems and methods described above may be provided as one or more computer-readable programs or executable instructions embodied on or in one or more articles of manufacture. The article of manufacture may be a floppy disk, a hard disk, a CD-ROM, a flash memory card, a PROM, a RAM, a ROM, or a magnetic tape. In general, the computer-readable programs may be implemented in any programming language, such as LISP, PERL, C, C++, C#, PROLOG, or in any byte code language such as JAVA. The software programs or executable instructions may be stored on or in one or more articles of manufacture as object code.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

We claim:

1. A method for screening an unconstrained subject, comprising:
    (a) transmitting, in sequence by each of a plurality of transmitters spatially distributed on two sides along a path of movement of a subject, radiation to be scattered from the subject;
    (b) collecting, by a plurality of sensors spatially distributed on the two sides and coherently configured with respect to the plurality of transmitters, measurements of scattered radiation corresponding to the radiation transmitted by each of the plurality of transmitters, such that:
  (i) at least a first one of the plurality of sensors collecting measurements of scattered radiation transmitted by at least one of the plurality of transmitters located on an opposite side of the path of movement as that on which the at least first one of the plurality of sensors is located, to produce a cross-path measurement, and
  (ii) at least a second one of the plurality of sensors collecting measurements of scattered radiation transmitted by at least one of the plurality of transmitters located on a same side of the path of movement as that on which the at least second one of the plurality of sensors is located, to produce a side-view measurement;
(c) generating, based on both the collected cross-path and side-view measurements, a two-dimensional or three-dimensional reconstruction estimate of body surface of the subject with one or more foreign objects on the subject; and
(d) detecting and identifying, based on the two-dimensional or three-dimensional reconstruction estimate of the body outline, surface or volume, one or more foreign objects on the subject.

2. The method of claim 1, wherein (a) comprises transmitting radiation at a first time instance by a first transmitter located on a first side of the two sides along the path of movement, and transmitting radiation at a second time instance by a second transmitter located on a second side of the two sides along the path of movement.

3. The method of claim 1, wherein (b) comprises collecting, at a first time instance by a first sensor located on a first side of the two sides along the path of movement, a measurement of a first scattered radiation corresponding to radiation transmitted by a first transmitter of the plurality of transmitters, and collecting, at the first time instance by a second sensor located on a second side of the two sides along the path of movement, a measurement of a second scattered radiation corresponding to radiation transmitted by the first transmitter.

4. The method of claim 1, wherein (b) comprises collecting, by the plurality of sensors, measurements of radiation scattered from the subject at a first position along the path of movement based on radiation from a first transmitter of the plurality of transmitters, and measurements of radiation scattered from the subject at a second position along the path of movement based on radiation from a second transmitter of the plurality of transmitters.

5. The method of claim 1, wherein (b) comprises collecting, by a first sensor, measurement of radiation scattered from the subject based on radiation transmitted by a first transmitter, the first transmitter and the first sensor having a subtended angle of at least 90 degrees relative to the subject.

6. The method of claim 1, wherein (b) comprises collecting, by a first sensor, measurement of radiation scattered from the subject based on radiation transmitted by a first transmitter, the first transmitter and the first sensor having a subtended angle less than 90 degrees relative to the subject.

7. The method of claim 1, further comprising:
  transmitting, at a first time instance by a first transmitter located in front of the subject or behind the subject along the path of movement, radiation incident on the subject, and
  collecting, by the plurality of sensors, measurements of radiation scattered from the subject corresponding to the radiation transmitted by the first transmitter.

8. The method of claim 1, wherein (c) comprises generating a plurality of partial reconstruction estimates, each of the plurality of partial reconstruction estimates generated based on measurements of scattered radiation corresponding to radiation transmitted by a respective transmitter from the plurality of transmitters.

9. The method of claim 8, further comprising registering a position of the subject along the path of movement with a corresponding one of the plurality of partial reconstruction estimates.

10. The method of claim 8, further comprising combining the plurality of partial reconstruction estimates to generate the two-dimensional or three-dimensional reconstruction estimate.

11. A system for screening an unconstrained subject, the system comprising:
  a plurality of transmitters spatially distributed on two sides along a path of movement of a subject, each of the plurality of transmitters transmitting, in sequence, radiation to be scattered from the subject;
  a plurality of sensors spatially distributed on the two sides and coherently configured with respect to the plurality of transmitters, the plurality of sensors collecting measurements of scattered radiation corresponding to the radiation transmitted by each of the plurality of transmitters, such that:
    (i) at least a first one of the plurality of sensors collecting measurements of scattered radiation transmitted by at least one of the plurality of transmitters located on an opposite side of the path of movement as that on which the at least first one of the plurality of sensors is located, to produce a cross-path measurement, and
    (ii) at least a second one of the plurality of sensors collecting measurements of scattered radiation transmitted by at least one of the plurality of transmitters located on a same side of the path of movement as that on which the at least second one of the plurality of sensors is located, to produce a side-view measurement; and
  an imaging module, executable by a processor, the imaging module (i) generating, based on both the collected cross-panel and side-view measurements, a two-dimensional or three-dimensional reconstruction estimate of body surface of the subject with one or more attached foreign objects, and (ii) detecting and identifying, based on the two-dimensional or three-dimensional reconstruction estimate of the body outline, surface or volume, one or more foreign objects on the subject.

12. The system of claim 11, wherein the plurality of transmitters comprises a first transmitter located on a first side of the two sides transmitting radiation at a first time instance, and a second transmitter located on a second side of the two sides transmitting radiation at a second time instance.

13. The system of claim 11, wherein the plurality of sensors comprises a first sensor located on a first side of the two sides collecting, at a first time instance, a measurement of a first scattered radiation corresponding to radiation transmitted by a first transmitter of the plurality of transmitters, and a second sensor located on a second side of the two sides collecting, at the first time instance, a measurement of a second scattered radiation corresponding to radiation transmitted by the first transmitter.

14. The system of claim 11, wherein the plurality of sensors collects measurements of radiation scattered from the subject at a first position along the path of movement based on radiation from a first transmitter of the plurality of transmitters, and collects measurements of radiation scattered from the subject at a second position along the path of movement based on radiation from a second transmitter of the plurality of transmitters.

15. The system of claim 11, wherein the plurality of sensors comprises a first sensor collecting measurement of radiation scattered from the subject based on radiation transmitted by a first transmitter, the first transmitter and the first sensor having a subtended angle of at least 90 degrees relative to the subject.

16. The system of claim 11, wherein the plurality of sensors comprises a first sensor collecting measurement of radiation scattered from the subject based on radiation transmitted by a first transmitter, the first transmitter and the first sensor having a subtended angle less than 90 degrees relative to the subject.

17. The system of claim 11, wherein the plurality of transmitters comprises a first transmitter located in front of the subject or behind the subject along the path of movement, the first transmitter transmitting, at a first time instance, radiation incident on the subject, and wherein the plurality of sensors collects measurements of radiation scattered from the subject corresponding to the radiation transmitted by the first transmitter.

18. The system of claim 11, wherein the imaging module generates a plurality of partial reconstruction estimates, each of the plurality of partial reconstruction estimates generated based on measurements of scattered radiation corresponding to radiation transmitted by a respective transmitter from the plurality of transmitters.

19. The system of claim 18, wherein the imaging module registers a position of the subject along the path of movement with a corresponding one of the plurality of partial reconstruction estimates.

20. The system of claim 18, wherein the imaging module combines the plurality of partial reconstruction estimates to generate the two-dimensional or three-dimensional reconstruction estimate.

* * * * *